United States Patent [19]

Steinmann

[11] Patent Number: 5,637,714

[45] Date of Patent: Jun. 10, 1997

[54] ORGANIC COMPOSITIONS STABILIZED WITH ADDUCTS OF HINDERED AMINE-EPOXIDES

[75] Inventor: Alfred Steinmann, Praroman, Switzerland

[73] Assignee: Ciba-Geigy Corporation, Tarrytown, N.Y.

[21] Appl. No.: 475,130

[22] Filed: Jun. 7, 1995

Related U.S. Application Data

[62] Division of Ser. No. 271,706, Jul. 7, 1994, Pat. No. 5,457,204.

[30] Foreign Application Priority Data

Jul. 13, 1993 [CH] Switzerland .................. 2097/93

[51] Int. Cl.$^6$ ..................... C07D 211/46
[52] U.S. Cl. ............. 546/242; 525/99; 525/100; 544/215; 544/221; 544/222; 546/186; 546/187; 546/190; 546/191; 546/216; 546/217
[58] Field of Search ............ 525/99, 100; 544/215, 544/221, 222; 546/186, 187, 190, 191, 216, 217, 242

[56] References Cited

U.S. PATENT DOCUMENTS

| | | | |
|---|---|---|---|
| 4,405,737 | 9/1983 | Hirai et al. | 524/102 |
| 4,537,923 | 8/1985 | Slongo et al. | 524/100 |
| 5,051,511 | 9/1991 | Seltzer et al. | 546/242 |
| 5,145,893 | 9/1992 | Galbo et al. | 524/99 |
| 5,169,949 | 12/1992 | Wright | 546/242 |

FOREIGN PATENT DOCUMENTS

| | | |
|---|---|---|
| 0001835 | 6/1979 | European Pat. Off. |
| 0097616 | 1/1984 | European Pat. Off. |
| 0518807 | 12/1992 | European Pat. Off. |
| 0526399 | 2/1993 | European Pat. Off. |

*Primary Examiner*—Yogendra N. Gupta
*Attorney, Agent, or Firm*—Michele A. Kovaleski

[57] ABSTRACT

Esters or phenol ethers of the formula I or II

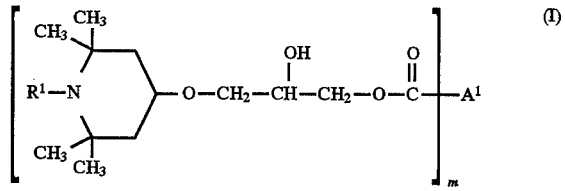

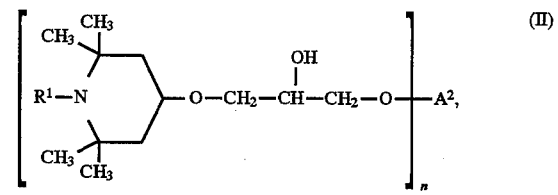

in which m and n are each an integer from the range from 1 to 6;

$A^1$ is an m-valent hydrocarbon radical having 1 to 30 carbon atoms; or an m-valent hydrocarbon radical having 2 to 30 carbon atoms, which contains the heteroatoms oxygen, nitrogen and/or sulfur and the free valencies of which are located on carbon atoms; and in which $A^1$, in the case where m=2, additionally is a direct bond;

$A^2$ is an n-valent aromatic or araliphatic hydrocarbon radical having 6 to 30 carbon atoms; or an n-valent aromatic or araliphatic hydrocarbon radical having 5 to 30 carbon atoms, which contains the heteroatoms oxygen, nitrogen and/or sulfur and n free valencies of which are located on those carbon atoms which are a constituent of aromatic rings;

$R^1$ is hydrogen; a hydrocarbon or hydrocarbonoxy radical having 1 to 36 carbon atoms, which is unsubstituted or substituted by —CO—N($R^3$)$_2$ or interrupted by —CON($R^3$)— or —N($R^3$)—CO— or 1 or 6 oxygen or sulfur atoms; benzoyl or napthoyl, each of which is substituted by 1 to 3 $C_1$–$C_4$alkyl or $C_1$–$C_4$alkoxy radicals; or —CO—$R^2$; in which $R^2$ is $C_1$—$C_{18}$alkyl; $C_5$–$C_8$cycloalkyl; phenyl; naphthyl; $C_7$–$C_9$phenylalkyl; or $C_{11}$–$C_{14}$naphthylalkyl; and $R^3$ has the same meanings as $R^2$ or is hydrogen, are described.

The compounds are suitable for stabilizing organic material against the damaging influence of light, oxygen and/or heat.

6 Claims, No Drawings

ORGANIC COMPOSITIONS STABILIZED WITH ADDUCTS OF HINDERED AMINE-EPOXIDES

This is a divisional of Ser. No. 08/271,706, filed Jul. 7, 1994 now U.S. Pat. No. 5,457,204.

The invention relates to novel compounds which can be obtained by reaction of hindered amines containing epoxide groups with phenols or carboxylic acids, their use as stabilizers of organic material against the damaging influence of light, oxygen and/or heat, and the corresponding stabilized compositions.

The preparation of some compounds of the 2,2,6,6-tetramethyl-4-(2,3-epoxypropoxy)piperidine type and their use as stabilizers for organic polymers is described, for example, by Luston and Vass, Makromol. Chem., Macromol. Symp. 27, 231 (1989).

Reaction products of these epoxides with toluenesulfonic acid and ethylenedisulfonic acid, and combined use thereof as curing catalysts and light stabilizers in paints are mentioned in EP-A-097616.

The bonding of reactive polyalkylpiperidines to fluorine polymers which contain free carboxyl groups is described in EP-A-526 399.

The publication EP-A-001835 discloses further reaction of the piperidines containing epoxide groups with dicarboxylic acid anhydrides to give polyesters.

There continues to be a need for novel stabilizers of the tetraalkyl-4-(2,3-epoxypropoxy)piperidine type having improved use properties.

The invention therefore firstly relates to esters of the formula I

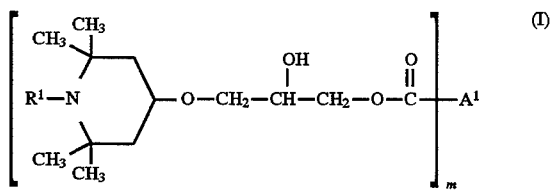

or phenol ethers of the formula II

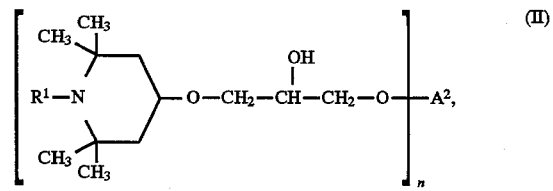

in which m and n are each an integer from the range from 1 to 6;

$A^1$ is an m-valent hydrocarbon radical having 1 to 30 carbon atoms; or an m-valent hydrocarbon radical having 2 to 30 carbon atoms, which contains the heteroatoms oxygen, nitrogen and/or sulfur and the free valencies of which are located on carbon atoms; and in which $A^1$, in the case where m=2, additionally is a direct bond;

$A^2$ is an n-valent aromatic or araliphatic hydrocarbon radical having 6 to 30 carbon atoms; or an n-valent aromatic or araliphatic hydrocarbon radical having 5 to 30 carbon atoms, which contains the heteroatoms oxygen, nitrogen and/or sulfur and n free valencies of which are located on those carbon atoms which are a constituent of aromatic rings;

$R^1$ is hydrogen; a hydrocarbon or hydrocarbonoxy radical having 1 to 36 carbon atoms, which is unsubstituted or substituted by —CO—N($R^3$)$_2$ or interrupted by —CO—N($R^3$)— or —N($R^3$)—CO— or 1 to 6 oxygen or sulfur atoms; benzoyl or naphthoyl, each of which is substituted by 1 to 3 $C_1$-$C_4$alkyl or $C_1$-$C_4$alkoxy radicals; or —CO—$R^2$; in which $R^2$ is $C_1$-$C_{18}$alkyl; $C_5$-$C_8$cycloalkyl; phenyl; naphthyl; $C_7$-$C_9$phenylalkyl; or $C_{11}$-$C_{14}$naphthylalkyl; and $R^3$ has the same meanings as $R^2$ or is hydrogen.

The compounds of the formula I and II can advantageously be employed for stabilizing organic material against the damaging influence of light, oxygen and/or heat.

In an m-valent hydrocarbon radical $A^1$ having 2 to 30 carbon atoms which contains the heteroatoms oxygen, nitrogen and/or sulfur, these are as a rule in the form of —O—, tertiary—OH, —N($R^2$)—,

and/or —S—; in an n-valent aromatic or araliphatic hydrocarbon radical $A^2$ having 5 to 30 carbon atoms which contains the heteroatoms oxygen, nitrogen and/or sulfur, these are as a rule in the form of —O—, tertiary—OH, —N($R^2$)—,

and/or —S—. Aryl stands for an aromatic hydrocarbon residue such as, for example, phenyl or naphthyl. Aralkyl means alkyl which is substituted by an aromatic hydrocarbon residue, e.g. a hydrocarbon residue having 6 to 10 carbon atoms; examples for aralkyl include benzyl and α-methylbenzyl.

The di- and trivalent heteroatoms mentioned can bond to the same adjacent atom or to different adjacent atoms; the adjacent atoms are as a rule carbon atoms. Thus, for example, —O— can form an ether or a carbonyl group. The same applies correspondingly to —S— and

thus,

can be, for example, a constituent of a tertiary aliphatic amine, of a ring structure, for example pyridine, or of a cyano group. A tertiary hydroxyl group is to be understood as meaning a substituent of the type —OH on a tertiary carbon atom. This is distinguished by the fact that it bonds with its other three free valencies to three further carbon atoms; the resulting compounds are also called tertiary alcohols (cf. Beyer/Walter, Lehrbuch der Organischen Chemie (Textbook of Organic Chemistry), 20th Edition, pages 59 and 111, S. Hirzel Verlag, Stuttgart 1984). A radical which contains a tertiary hydroxyl group therefore contains at least 4 carbon atoms.

Alkyl or alkylene $A^1$, $A^2$ or $R^1$ as defined which is interrupted by —O—, —S—,

—CO—N(R³)—, —N(R³)CO— or —N(R²)— is alkyl or alkylene having at least 2, preferably at least 4, carbon atoms, which is preferably interrupted by 1–6 —O— or —S— groups or 1–3

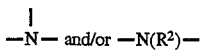

groups, in particular by 1–6 —O—, or 1–2 —S—,

or —N(R²)—; the heteroatoms or carbonyl groups preferably bond to saturated carbon atoms and not to other heteroatoms or carbonyl groups; peroxo or hydrazine structures as a rule do not occur. Polyoxyethylene chains, the ends of which are terminated by $C_1$–$C_8$alkyl, are examples of a possible definition of these radicals.

Two radicals of the same type in the same formula can be identical or different; for example, one of the two radicals R³ in the part formula —CO—N(R³)₂ can be hydrogen, while the other radical R³ has one of the meanings of R².

A monovalent radical A¹ is defined, for example, as follows:

branched or unbranched alkyl, such as methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl, docosyl, pentacosyl or triacosyl; unbranched alkyl is preferred and unbranched $C_6$–$C_{18}$alkyl is particularly preferred; branched or unbranched $C_2$–$C_{30}$alkenyl such as vinyl, α-methylvinyl, propenyl (allyl), butenyl, pentenyl, hexenyl, heptenyl, octenyl, nonenyl, decenyl, dodecenyl, pentadecenyl or octadecenyl;

alkyl substituted by $C_5$–$C_8$cycloalkyl, such as cyclopentylmethyl, cyclohexylmethyl, cycloheptylmethyl, cyclooctylmethyl, cyclohexylethyl, 2-cyclohexyl-n-propyl, 3-cyclohexyl-n-propyl or 4-cyclohexyl-n-butyl;

$C_2$–$C_{25}$alkyl which is interrupted by $C_5$–$C_8$cycloalkyl or one or more, preferably 1–3, of the groups —S—, —O— and/or —NR²—, for example of the formulae

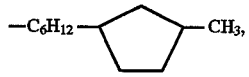

—CH₂—S—C₄H₉, —C₂H₄—O—C₂H₄—O—C₁₂H₂₅ or C₁₈H₃₆—N(C₄H₉)₂;

$C_5$–$C_8$cycloalkyl or $C_6$–$C_8$cycloalkenyl which is unsubstituted or substituted by $C_1$–$C_{12}$alkyl or $C_2$–$C_{12}$alkenyl, such as cyclopentyl, cyclohexyl, cycloheptyl, cyclooctyl, 2- or 4-methylcyclohexyl, dimethylcyclohexyl, trimethylcyclohexyl, t-butylcyclohexyl, 2-cyclohexenyl, 3-cycloheptenyl, cyclooctatetraenyl or 4-tert-butyl-cyclohex-2-enyl, preferably cyclohexyl and cyclohexenyl, in particular cyclohexyl;

$C_6$–$C_{10}$bicycloalkenyl, for example bicyclo-(2,2,1)-hepta-5-en-2-yl;

$C_7$–$C_{12}$phenylalkyl, $C_7$–$C_{12}$phenylalkenyl, $C_{11}$–$C_{16}$naphthylalkyl, $C_{11}$–$C_{16}$naphthylalkenyl, $C_{13}$–$C_{18}$biphenylalkyl or $C_{13}$–$C_{18}$biphenylalkenyl, for example $C_1$–$C_6$alkyl or $C_2$–$C_6$alkenyl which is substituted by phenyl, naphthyl or biphenyl, for example benzyl, phenethyl, β-phenylvinyl, 3-phenylpropyl, α-methylbenzyl, α,α-dimethylbenzyl, 2-phenylethenyl, 1-phenylprop-2-enyl, 6-phenylhexyl, 1-naphthylmethyl, 2-naphthylmethyl, 1-naphthyleth-1-yl, 2-(4-biphenylyl)-prop-2-yl or 1-(4-biphenylyl)-pent-3-en-1-yl.

Monovalent araliphatic or aromatic radicals A¹ and A² are defined, for example, as follows:

phenyl, naphthyl, biphenyl, triazinyl, 2,4-diphenyl-1,3,5-triazin-6-yl-phenyl, benzoylphenyl, benzylphenyl, α-methylbenzylphenyl or α,α-dimethylbenzylphenyl;

phenyl, naphthyl, biphenyl, triazinyl, 2,4-diphenyl-1,3,5-triazin-6-yl-phenyl, benzoylphenyl, benzylphenyl, α-methylbenzylphenyl or α,α-dimethylbenzylphenyl which is substituted by $C_1$–$C_{12}$alkyl or $C_2$–$C_{12}$alkenyl, such as methylphenyl, dimethylphenyl, trimethylphenyl, ethylphenyl, vinylphenyl, diethylphenyl, isopropylphenyl, tert-butylphenyl, di-tert-butylphenyl, methyl-di-t-butylphenyl, 1,1,3,3-tetramethylbutylphenyl and 1,1,3,3,5,5-hexamethylhexylphenyl, dodecenylphenyl, 1-methylnaphthyl, 2-methylnaphthyl, 1-ethylnaphthyl, 2-propyl-biphenyl-4-yl or 4-(1-hex-3-enyl)-biphenyl-8-yl; preferably phenyl, which is unsubstituted or substituted by 1–3, for example 1–2, in particular 1, $C_1$–$C_4$alkyl group(s), in particular methyl.

The divalent (for m=2 or n=2), trivalent (for m=3 or n=3), tetravalent (for m=4 or n=4), pentavalent (for m=5 or n=5) and hexavalent radicals A¹ and A² (for m=6 or n=6) are derived from the monovalent radicals defined above. A divalent radical differs from the corresponding monovalent radical in that it contains an open bond instead of a hydrogen atom; a trivalent radical differs from the corresponding monovalent radical in that it contains two open bonds instead of two hydrogen atoms; a tetravalent radical differs from the corresponding monovalent radical in that it contains three open bonds instead of three hydrogen atoms; a pentavalent radical differs from the corresponding monovalent radical in that it contains four open bonds instead of four hydrogen atoms; a hexavalent radical differs from the corresponding monovalent radical in that it contains five open bonds instead of five hydrogen atoms. Thus, for example, a divalent radical A¹ as defined can also be methylene, ethylene, —CH₂—C(CH₃)₂—CH₂—, prop-2-en-ylidene, 1,3-propylene, 1,4-butylene, 1,5-pentylene, 1,6-hexylene,

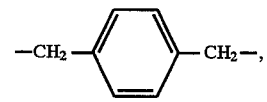

-continued $-CH_2-S-CH_2-$, $-C_2H_4-S-C_2H_4-$ or $-C_2H_4-O-C_2H_4-$, or cyclohexylene; a trivalent radical $A^1$ as defined can be, for example,

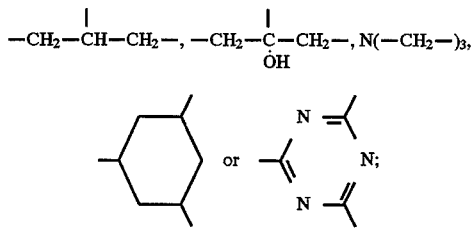

a tetravalent radical $A^1$ as defined can be, for example,

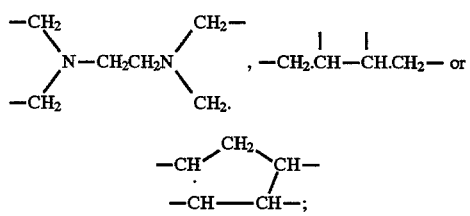

common possible definitions for divalent radicals $A^1$ and $A^2$ are, for example, o-, m- or p-phenylene, $-C_6H_4-C(CH_3)_2-C_6H_4-$, $-C_6H_4-CO-C_6H_4-$; for trivalent radicals $A^1$ and $A^2$ are, for example,

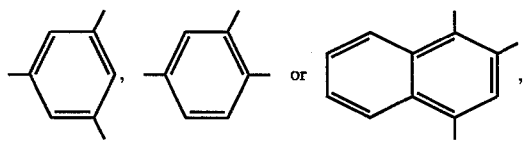

or for a tetravalent radical $A^1$ and $A^2$ are, for example,

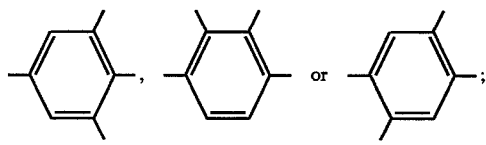

$A^2$ can be derived, for example, from an n-valent phenol of the formula

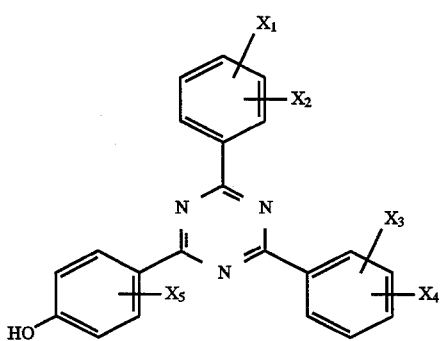

in which $X_1$ to $X_5$ independently of one another can be hydrogen, methyl or OH.

As described above, the $[-O-CO]_m-A^1$ group in formula I is derived from an m-basic carboxylic acid. This can be an aromatic, aliphatic or mixed aromatic-aliphatic acid, cycloaliphatic and bicycloaliphatic acids and/or unsaturated acids being expressly included. The acids can be, for example, the following:

caprylic acid, acetic acid, stearic acid, polyisobutenylsuccinic acid, n-hexacosanoic acid, trimethylacetic acid, propionic acid, isovaleric acid, lauric acid, oleic acid, acrylic acid, methacrylic acid, sorbic acid, linolenic acid, maleic acid, itaconic acid, glutaconic acid, dibasic acids, such as oxalic, malonic, dibutylmalonic, dibenzylmalonic, succinic, iso-dodecylsuccinic, glutaric, adipic, pimelic, suberic, azelaic or sebacic acid, the polymers of fatty acids, such as the dimers and trimers thereof, of the type described, for example, in Ind. and Eng. Chem. 33, 86–89 (1941), butane-1,2,3,4-tetracarboxylic acid, acids containing heteroatoms, for example thiodiglycolic acid, citric acid, nitrilotriacetic acid, ethylenediaminetetraacetic acid and 1,3,5-triazine-2,4,6-tricarboxylic acid, cycloaliphatic acids, such as cyclohexanecarboxylic acid, 1,2- and 1,4-cyclohexanedicarboxylic acid and naphthenic acids, including, for example, cyclopentanecarboxylic acid, cyclopentane-1,2,3,4-tetracarboxylic acid, cyclopentylacetic acid, 3-methylcyclopentylacetic acid, camphor acid, 4-methylcyclohexanecarboxylic acid and 2,4,6-trimethylcyclohexanecarboxylic acid, bicyclo[2.2.2]octa-5-ene-2,3-dicarboxylic acid and bicyclo[2.2.1]hepta-5-ene-2-carboxylic acid, aromatic carboxylic acids, such as benzoic acid, benzoylbenzoic acid, o-, m- and p-toluylic acid, phthalic acid, terephthalic acid, trimellitic acid, trimesic acid, pyromellitic acid, 1,2,4,5-benzenetetracarboxylic acid, diphenic acid, 1-naphthoic acid, 2-naphthoic acid, naphthalene-1,8-dicarboxylic acid, naphthalene-1,4-dicarboxylic acid, naphthalene-1,4,5-tricarboxylic acid and the like, paraffinic ω-aryl acids, such as phenylacetic acid, hydrocinnamic acid, phenylbutyric acid, γ-(1-naphthyl) butyric acid, δ-phenylene-n-valeric acid, ε-phenyl-n-caproic acid, o-, m- or p-phenylenediacetic acid or o-phenyleneacetic-β-propionic acid, and unsaturated phenyl acids, for example cinnamic acid.

$R^1$ is defined, for example, as follows:

branched or unbranched $C_1-C_{36}$alkyl such as methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl, docosyl, pentacosyl or triacosyl; unbranched alkyl is preferred and unbranched $C_1-C_{18}$alkyl is particularly preferred; branched or unbranched $C_1-C_{36}$alkyloxy, in particular $C_6-C_{18}$alkyloxy such as hexyloxy, heptyloxy, octyloxy, nonyloxy, decyloxy, undecyloxy or dodecyloxy;

$C_3-C_{36}$alkenyl such as propenyl (allyl), butenyl, pentenyl, hexenyl, heptenyl, octenyl, nonenyl, decenyl, dodecenyl, pentadecenyl, octadecenyl; $C_3-C_{36}$alkenyloxy; $C_3-C_9$alkynyl, for example propargyl;

alkyl or alylkoxy which is substituted by $C_5-C_8$cycloalkyl, such as cyclopentylmethyl, cyclohexylmethyl, cycloheptylmethyl, cyclooctylmethyl, cyclohexylethyl, 2-cyclohexyl-n- propyl, 3-cyclohexyl-n-propyl, 4-cyclohexyl-n-butyl; alkyl or alkyloxy which is interrupted by $C_5$–$C_8$cycloalkyl or 1 to 6 —O—, for example of the formulae

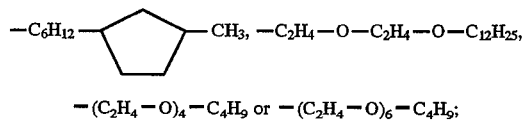

—(C$_2$H$_4$—O)$_4$—C$_4$H$_9$ or —(C$_2$H$_4$—O)$_6$—C$_4$H$_9$;

$C_5$–$C_8$cycloalkyl, $C_5$–$C_8$cycloalkyloxy, $C_6$–$C_8$cycloalkenyl or $C_6$–$C_8$cycloalkenyloxy, which is unsubstituted or substituted by $C_1$–$C_{12}$alkyl or $C_2$–$C_{12}$alkenyl, such as cyclopentyl, cyclopentyloxy, cyclohexyl, cyclohexyloxy, cycloheptyl, cycloheptyloxy, cyclooctyl, cyclooctyloxy, 2- or 4-methylcyclohexyloxy, dimethylcyclohexyloxy, trimethylcyclohexyl, t-butylcyclohexyl or 2-cyclohexenyl, in particular cyclohexyl and cyclohexyloxy;

phenyl, phenoxy, benzylphenyl or benzylphenyloxy;

phenyl or phenyloxy which is substituted by $C_1$–$C_{12}$alkyl or $C_2$–$C_{12}$alkenyl;

$C_7$–$C_{12}$phenylalkyl, $C_7$–$C_{12}$phenylalkenyl, $C_7$–$C_{12}$phenylalkyloxy, $C_7$–$C_{12}$phenylalkenyloxy, for example benzyl, benzyloxy, phenethyloxy, 3-phenylpropyloxy, α-methylbenzyl, α-methylbenzyloxy, α,α-dimethylbenzyl or α,α-dimethylbenzyloxy.

Preferred compounds of the formulae I and II are those in which m and n independently of one another are a number from the range from 1 to 4, and in particular those in which m is a number from the range from 1 to 4 and n is a number from the range from 1 to 3. Compounds of the formulae I and II which are of particular intererest are those in which m and n are 1 or 2, in particular 2.

Preferred compounds of the formula I and II are those in which m and n are 1, 2, 3 or 4;

$A^1$, in the case where m=1, is $C_1$–$C_{25}$alkyl, which is unsubstituted or substituted by $C_5$–$C_8$cycloalkyl; or $C_2$–$C_{25}$alkyl, which is interrupted by $C_5$–$C_8$cycloalkyl, —S—, —O— or —NR$^2$— or various of these groups; or $A^1$, in the case where m=1, is $C_5$–$C_8$cycloalkyl, which is unsubstituted or substituted by $C_1$–$C_{12}$alkyl; $C_6$–$C_8$cycloalkenyl, which is unsubstituted or substituted by $C_1$–$C_{12}$alkyl;

phenyl, which is unsubstituted or substituted by 1 to 3 $C_1$–$C_4$alkyl, $C_2$–$C_4$alkenyl or $C_1$–$C_4$alkoxy radicals and/or a group of the formula

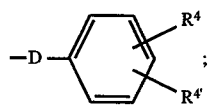

or $C_2$–$C_{25}$alkenyl;

$C_3$–$C_{25}$alkenyl which is interrupted by —O—;

$C_7$–$C_{12}$phenylalkyl, which is unsubstituted or substituted by $C_1$–$C_4$alkyl or $C_2$–$C_4$alkenyl or $C_1$–$C_4$alkoxy;

$A^1$, in the case where m=2, is a direct bond; $C_1$–$C_{18}$alkylene; $C_2$–$C_{18}$alkenylene;

$C_5$–$C_8$cycloalkylene, which is unsubstituted or substituted by $C_1$–$C_{12}$alkyl;

$C_6$–$C_8$cycloalkenylene, which is unsubstituted or substituted by $C_1$–$C_{12}$alkyl; phenylene, which is unsubstituted or substituted by 1 or 2 $C_1$–$C_4$alkyl, $C_2$–$C_4$alkenyl or $C_1$–$C_4$alkoxy radicals and/or a group of the formula

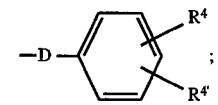

a divalent radical of the formula

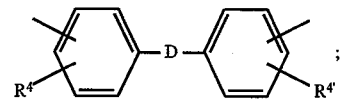

a divalent heterocyclic radical from the group consisting of furan, thiophene and pyrrole, which is substituted on the nitrogen atom by hydrogen or the substituent —R$^2$; or $A^1$, in the case where m=2, is $C_2$–$C_{18}$alkylene which is interrupted by $C_5$–$C_8$cycloalkylene, phenylene, —S—, —O— or —NR$^2$— or various of these groups; and $A^1$, in the case where m=3, is $C_1$–$C_8$alkanetriyl; $C_2$–$C_8$alkenetriyl; benzenetriyl; a trivalent radical of the formula

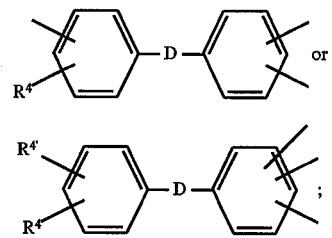

a trivalent group of the formula

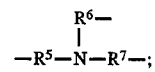

1,3,5-triazine-2,4,6-triyl;

$C_5$–$C_8$cycloalkanetriyl; or $C_2$–$C_{18}$alkanetriyl which is interrupted by —S—, —O— or —NR$^2$— and/or substituted by tertiary —OH;

$A^1$, in the case where m=4, is a benzene, cyclopentyl or cyclohexyl radical having 4 free valencies or a tetravalent radical of formula

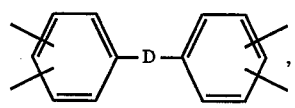

a tetravalent radical of the formula

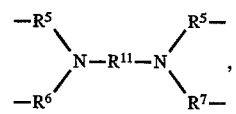

or $C_1$–$C_8$alkanetetrayl;

$A^2$, in the case where n=1, is phenyl, which is unsubstituted or substituted by 1 to 3 $C_1-C_4$alkyl, $C_2-C_4$alkenyl or $C_1-C_4$alkoxy radicals and/or a group of the formula

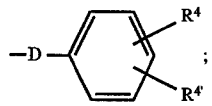

a triazinylphenyl radical of the formula

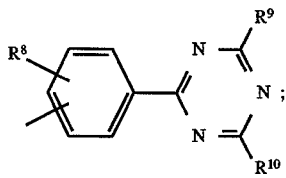

or naphthyl;

$A^2$, in the case where n=2, is phenylene, which is unsubstituted or substituted by 1 or 2 $C_1-C_4$alkyl, $C_2-C_4$alkenyl or $C_1-C_4$alkoxy radicals and/or a group of the formula

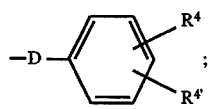

a divalent radical of the formula

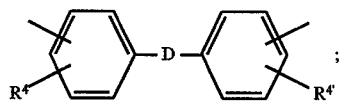

or naphthylene;

$A^2$, in the case where n=3, is benzenetriyl; or a trivalent radical of the formula

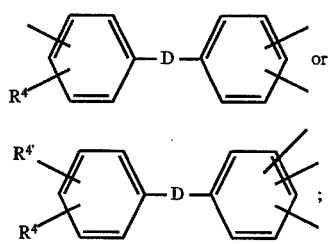

$A^2$, in the case where n=4, is a benzene radical having 4 free valencies or a tetravalent radical of the formula

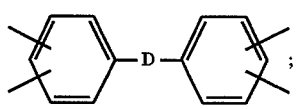

or $A^2$ is an n-valent triphenyltriazinyl radical of the formula

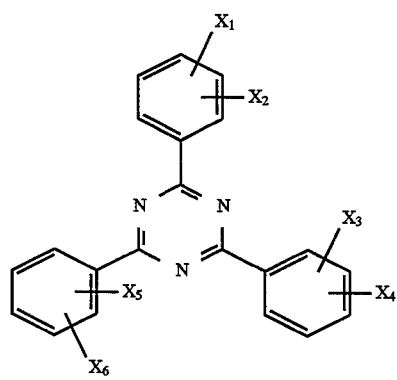

in which 1 to 4 of the radicals $X_1$ to $X_6$ in each case are an open bond and the others, independently of one another, are hydrogen or $C_1-C_4$alkyl;

D is a direct bond; $C_1-C_{10}$alkylene; or one of the groups —CO—, —S—, —O— or —$SO_2$—;

$R^1$ is $C_1-C_{36}$alkyl; $C_3-C_{36}$alkenyl; $C_3-C_9$alkynyl; $C_1-C_{36}$alkoxy; $C_3-C_{36}$alkenyloxy;

$C_5-C_{12}$cycloalkyl, which is unsubstituted or substituted by 1 to 3 $C_1-C_4$alkyl or $C_1-C_4$alkoxy radicals; $C_5-C_{12}$cycloalkoxy, which is unsubstituted or substituted by 1 to 3 $C_1-C_4$alkyl or $C_1-C_4$alkoxy radicals; phenyl, which is unsubstituted or substituted by 1 to 3 $C_1-C_4$alkyl or $C_1-C_4$alkoxy radicals; naphthyl, which is unsubstituted or substituted by 1 to 3 $C_1-C_4$alkyl or $C_1-C_4$alkoxy radicals; phenoxy, which is unsubstituted or substituted by 1 to 3 $C_1-C_4$alkyl or $C_1-C_4$alkoxy radicals; naphthoxy, which is unsubstituted or substituted by 1 to 3 $C_1-C_4$alkyl or $C_1-C_4$alkoxy radicals; $C_7-C_{12}$phenylalkyl, which is unsubstituted or substituted on the phenyl ring by 1 to 3 $C_1-C_4$alkyl or $C_1-C_4$alkoxy radicals; $C_7-C_{12}$phenylalkoxy, which is unsubstituted or substituted on the phenyl ring by 1 to 3 $C_1-C_4$alkyl or $C_1-C_4$alkoxy radicals; or —CO—$R^2$; in which $R^2$ is $C_1-C_{18}$alkyl; $C_5-C_8$cycloalkyl; phenyl; naphthyl; $C_7-C_9$phenylalkyl; or $C_{11}-C_{14}$naphthylalkyl; and $R^3$ has the same meanings as $R^2$ or is hydrogen;

$R^4$ and $R^{4'}$ independently of one another are hydrogen or $C_1-C_4$alkyl;

$R^5$, $R^6$ and $R^7$ independently of one another are $C_1-C_3$alkylene;

$R^8$ is hydrogen or $C_1-C_4$alkyl;

$R^9$ and $R^{10}$ independently of one another are $C_3-C_{18}$alkyl or $C_5-C_8$cycloalkyl; and $R^{11}$ is $C_2-C_6$alkylene.

In the above formulae of the type

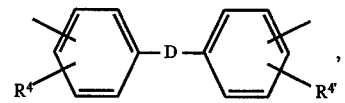

the lines projecting into the phenyl nucleus with the symbol $R^4$ or $R^{4'}$ are substituents which are in the o-, m- or p-position relative to the bridge member D; the lines without symbols designate open bonds to other positions in the o-, m- or p-position relative to D which are still free.

D is preferably one of the groups

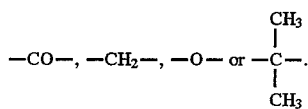

$R^4$ and $R^{4'}$ are preferably hydrogen, methyl or tert-butyl; in particular hydrogen.

$R^1$ is particularly preferably $C_1$–$C_6$alkyl, $C_6$–$C_{12}$alkoxy, cyclohexyl, cyclohexyloxy, cycloheptyloxy, cyclooctyloxy, $C_7$–$C_9$phenylalkyl or $C_7$–$C_9$phenylalkoxy; in particular methyl, cyclohexyloxy, benzyl, benzyloxy, α-methylbenzyl, α-methylbenzyloxy, octyloxy and dodecyloxy, in particular methyl, cyclohexyloxy, benzyl and octyloxy.

Compounds which are of particularly prominent interest are those of the formula I in which $A^1$ is m- or p-phenylene; 1,3,5-benzenetriyl; ethylene; 1,4-cyclohexylene; n-heptadecyl; n-undecyl; 1,6-hexylene; 1,8-octylene; 1,10-decylene or 1,12-dodecylene; in particular m-phenylene; ethylene; 1,8-octylene; 1,10-decylene; 1,4-cyclohexylene or n-undecyl, and those of the formula II in which $A^2$ is m-phenylene or a divalent radical of the formula

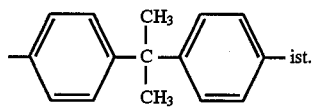

Preferred compounds of the formulae I and II are those in which $A^1$, in the case where m=1, is $C_6$–$C_{18}$alkyl; $C_2$–$C_{12}$alkenyl; cyclohexyl; cyclohexenyl; phenyl, which is unsubstituted or substituted by 1 to 3 $C_1$–$C_4$alkyl radicals or a group of the formula

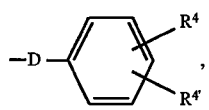

or $C_2$–$C_4$alkenyl; $C_3$–$C_{12}$alkenyl which is interrupted by —O—;

or $C_7$–$C_{12}$phenylalkyl, which is unsubstituted or substituted on the phenyl ring by $C_1$–$C_4$alkyl or $C_2$–$C_4$alkenyl or $C_1$–$C_4$alkoxy;

$A^1$, in the case where m=2, is a direct bond; $C_1$–$C_{18}$alkylene; $C_2$–$C_{18}$alkylene which is interrupted by —O— or —S—; $C_2$–$C_{18}$alkenylene; $C_5$–$C_9$cycloalkylene; phenylene, which is unsubstituted or substituted by 1 or 2 $C_1$–$C_4$alkyl or $C_1$–$C_4$alkoxy radicals and/or a group of the formula

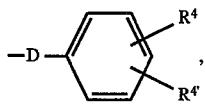

or $C_2$–$C_4$alkenyl; a divalent radical of the formula

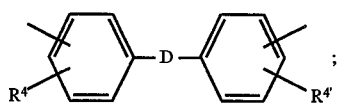

$A^1$, in the case where m=3, is $C_3$–$C_8$alkanetriyl; $C_3$–$C_8$alkanetriyl substituted by a tertiary hydroxyl group; benzenetriyl; $N[(CH_2)—]_3$; $C_5$–$C_8$cycloalkanetriyl; or 1,3,5-triazine-2,4,6-triyl;

$A^1$, in the case where m=4, is a benzene, cyclopentyl or cyclohexyl radical having 4 free valencies; or

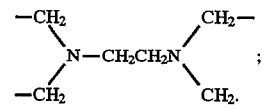

$A^2$, in the case where n=1, is phenyl, which is unsubstituted or substituted by $C_1$–$C_4$alkyl or a group of the formula

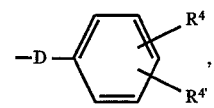

or $C_2$–$C_4$alkenyl; or naphthyl;

$A^2$, in the case where n=2, is phenylene, which is unsubstituted or substituted by $C_1$–$C_4$alkyl or a group of the formula

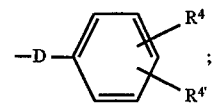

a divalent radical of the formula

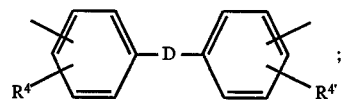

or naphthylene;

$A^2$, in the case where n=3, is benzenetriyl;

$A^2$, in the case where n=4, is a benzene radical having 4 free valencies;

or $A^2$ is an n-valent triphenyltriazinyl radical of the formula

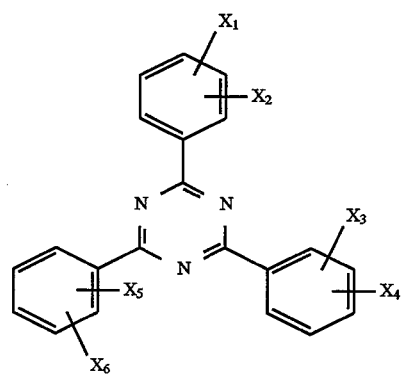

in which 1 to 4 of the radicals $X_1$ to $X_6$ in each case are an open bond and the others independently of one another are hydrogen or methyl;

D is a direct bond or one of the groups

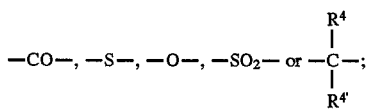

$R^1$ is $C_1$–$C_{18}$alkyl; $C_4$–$C_{22}$alkoxy; $C_3$–$C_8$alkenyl; $C_3$–$C_8$alkynyl; $C_5$–$C_8$cycloalkyl; $C_5$–$C_8$cycloalkoxy; $C_7$–$C_{12}$phenylalkyl; $C_7$–$C_{12}$phenylalkoxy; $C_1$–$C_8$alkanoyl; $C_3$–$C_5$alkenoyl; or benzoyl; and $R^4$ and $R^{4'}$ independently of one another are hydrogen or $C_1$–$C_4$alkyl.

Compounds of the formulae I and II which are of particular interest are those in which m and n are each integers from the range from 1 to 4;

$A^1$, in the case where m=1, is $C_6$–$C_{18}$alkyl;

$A^1$, in the case where m=2, is $C_2$–$C_{18}$alkylene; cyclohexylene; phenylene; a divalent radical of the formula

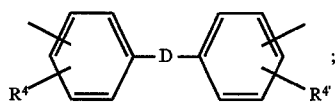

$A^1$, in the case where m=3, is benzenetriyl or cyclohexanetriyl; and $A^1$, in the case where m=4, is a benzene radical having 4 free valencies;

$A^2$, in the case where n=1, is phenyl, which is unsubstituted or substituted by $C_1$–$C_4$alkyl; or naphthyl;

$A^2$, in the case where n=2, is phenylene, which is unsubstituted or substituted by $C_1$–$C_4$alkyl or a group of the formula

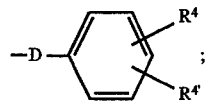

naphthylene; or a divalent radical of the formula

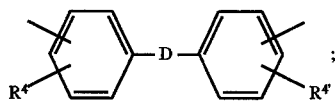

$A^2$, in the case where n=3, is benzenetriyl; and $A^2$, in the case where n=4, is a benzene radical having 4 free valencies;

D is one of the groups

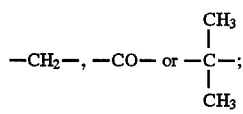

and $R^4$ and $R^{4'}$ independently of one another are hydrogen, methyl or tert-butyl.

Particularly preferred compounds of the formulae I and II are those in which m is an integer from the range from 1 to 4 and n is an integer from the range from 1 to 3;

$A^1$, in the case where m=1, is $C_{10}$–$C_{18}$alkyl;

$A^1$, in the case where m=2, is $C_2$–$C_{18}$alkylene; cyclohexylene; or phenylene;

$A^1$, in the case where m=3, is benzenetriyl or cyclohexanetriyl; and $A^1$, in the case where m=4, is benzenetetrayl;

$A^2$, in the case where n=1, is phenyl;

$A^2$, in the case where n=2, is phenylene or a divalent radical of the formula

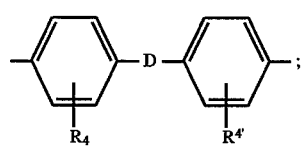

$A^2$, in the case where n=3, is benzenetriyl;

D is one of the groups

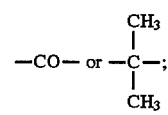

$R^1$ is $C_1$–$C_6$alkyl; $C_6$–$C_{12}$alkoxy; cyclohexyl; cyclohexyloxy; cycloheptyloxy; cyclooctyloxy; or $C_7$–$C_9$phenylalkyl; and $R^4$ and $R^{4'}$ independently of one another are hydrogen, methyl or tert-butyl.

Compounds of the formula I or of the formula II which are of particular importance are those which are derived from a carboxylic acid which is ethylenically unsaturated in the aliphatic moiety or a phenol derivative which is ethylenically unsaturated in the aliphatic moiety. Such compounds on the one hand have the stabilizing action described, and on the other hand can also be converted into high molecular weight stabilizers by polymerization and are thus useful intermediates for the preparation of polymeric light stabilizers.

Examples of such compounds are compounds of the formulae I and II in which m is 1 or 2 and n is 1;

$A^1$, in the case where m=1, is $C_2$–$C_{12}$alkenyl; cyclohexylene; phenyl, which is substituted by $C_2$–$C_4$alkenyl and may be substituted by $C_1$–$C_4$alkyl or a group of the formula

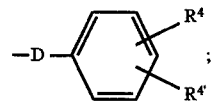

$C_3$–$C_{12}$alkenyl, which is interrupted by —O—; or $C_7$–$C_{12}$phenylalkyl which is substituted on the phenyl ring by $C_2$–$C_4$alkenyl;

$A^2$, in the case where m=2, is $C_2$–$C_{18}$alkenylene; or phenylene which is substituted on the phenyl ring by $C_2$–$C_4$alkenyl;

$A^2$, in the case where n=1, is phenyl which is substituted by $C_2$–$C_4$alkenyl;

D is a direct bond or one of the groups

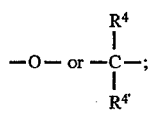

R¹ is $C_1$-$C_{18}$alkyl; $C_4$-$C_{22}$alkoxy; $C_5$-$C_8$cycloalkyl; $C_5$-$C_8$cycloalkoxy; $C_7$-$C_{12}$phenylalkyl; $C_1$-$C_8$alkanoyl; or benzoyl; and $R^4$ and $R^{4'}$ independently of one another are hydrogen or $C_1$-$C_4$alkyl.

The above derivatives of ethylenically unsaturated carboxylic acids and alkenylphenols which can particularly advantageously be employed are those in which m and n in each case are 1, and amongst these, in particular those in which $A^1$ is vinyl; α-methylvinyl; $C_1$-$C_4$alkyl substituted by vinyloxy; vinylphenyl or vinylbenzyl; and $A^2$ is vinylphenyl.

A preferred process for the preparation of a compound of the formula I or of the formula II, to which the invention likewise relates, starts from a piperidine compound of the formula III:

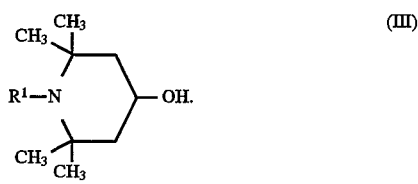

Compounds of the formula III are known, and some of them are obtainable commercially.

The piperidine compound of the formula III is first reacted with epichlorohydrin in a manner known per se, HCl being split off, to give the intermediate of the formula IV

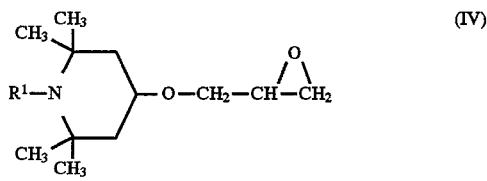

and this is then reacted (a) with a carboxylic acid of the formula V

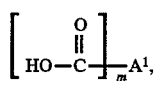

to form the ester of the formula I, or (b) with a phenol of the formula VI

to form the phenol ether of the formula II. The symbols m, n, $R^1$, $A^1$ and $A^2$ are as defined above.

The intermediate of the formula IV (epoxide) can be prepared by one of the methods described in EP-A-001835 or by Luston and Vass, Makromol. Chem., Macromol. Symp. 27, 231 (1989). Advantageously, an excess of epichlorohydrin is slowly added to the piperidine compound of the formula III in the presence of strong bases, for example aqueous concentrated alkali metal hydroxide solution, and if appropriate an organic solvent.

The base is advantageously employed in about a 2- to 20-fold molar excess based on the compound of the formula III; for example, 3–15 mol, preferably 4–12 mol, of sodium hydroxide or potassium hydroxide as a 50% aqueous solution are used per mol of piperidine compound. The amount of organic solvent is advantageously chosen such that the compound of the formula III is dissolved completely; suitable solvents are, for example, inert solvents, such as hydrocarbons or ethers; toluene is preferred.

1–4, preferably 1.2–3, in particular 1.5–2.5, equivalents of epichlorohydrin, for example, can be employed per equivalent of the piperidine compound of the formula Furthermore, 1–30 mol %, preferably 5–25 mol %, of a tertiary amine salt, for example a tetraalkylammonium halide, such as tetramethylammonium chloride or tetrabutylammonium bromide, or of a phosphonium salt, for example a quaternary phosphoniumhalide, such as ethyltriphenylphosphonium bromide, can advantageously be added to the mixture as a catalyst.

The temperature during the reaction is advantageously 0°–100° C., preferably 20°–80° C., in particular 30°–70° C.

When the reaction is complete, working up can be carded out by customary methods; advantageously, the mixture is first diluted with water, for example by adding the reaction mixture to 1 to 4 times the volume of ice-water; the organic phase can then be separated off directly or extracted, ethyl acetate, for example, being suitable for the extraction. After the organic phase has been dried, the product can be isolated by removal of the solvent. It is also possible to include further purification steps, such as dispersion of active charcoal, filtration or distillation.

Further reaction of the intermediate of the formula IV by opening the epoxide to give the compound of the formula I or II can be carded out with or without a solvent; solvents which can be employed, if appropriate, are polar or non-polar, inert and, in the case of formula II, preferably high-boiling. Thus, for example, aromatic or aliphatic hydrocarbons can be used, as can heterocyclic solvents, ethers, sulfones, sulfoxides or amides; preferred solvents are, inter alia, relatively high-boiling hydrocarbon fractions, such as ligroin or petroleum ether, aromatic hydrocarbons, such as toluene or xylene, decalin, cyclic or open-chain ethers, such as dibutyl ether or dioxane, dimethylformamide or dimethyl sulfoxide; toluene or xylene is particularly preferred.

The temperature of the reaction mixture can be kept in the boiling range (reflux) for the duration of the reaction. For this, a reaction mixture containing solvent is heated to the boiling point, in general under normal pressure, and the solvent which has evaporated is condensed with the aid of a suitable condenser and recycled to the reaction mixture. Where appropriate, the boiling range of the pure solvent can be in the range from 60° to 180° C., for example 60° to 140° C. If a carboxylic acid of the formula V is employed for the reaction, the temperature is preferably kept in the range from 30° to 130° C., in particular 40° to 90° C., and the duration of the reaction is, for example, 1 to 20 hours. If a phenol of the formula VI is employed, the temperature is preferably kept in the range from 80° to 180° C., in particular 100° to 160° C., and the duration of the reaction is, for example, 3 to 36 hours.

The reaction is preferably carded out under an inert gas, for example nitrogen or argon; the reaction mixture is advantageously stirred. The epoxide of the formula IV is preferably employed in about the equivalent amount or in a slight excess relative to the carboxylic acid groups of the reactant of the formula V or the phenolic hydroxyl groups of the reactant of the formula VI, for example in an amount of 1.0 to 1.3 equivalents, in particular 1.0 to 1.15 equivalents, per equivalent of phenolic OH or carboxylic acid.

The reaction is preferably carried out in the presence of a quaternary ammonium salt, for example a tetraalkylammonium halide, for example tetramethylammonium chloride or tetrabutylammonium bromide, or a phosphonium salt, for example a quaternary phosphonium halide, such as ethyltriphenylphosphonium bromide, as a catalyst. The catalyst is advantageously employed in an amount of 1 to 5 mol % relative to the compound of the formula IV.

Working up after the reaction has ended can be carried out by customary methods; for example, the cooled mixture is washed first with the aqueous solution of a base, for example very dilute alkali metal hydroxide solution, and then with water and, after drying, the solvent is removed, for example by applying reduced pressure and/or heating. After drying, further purification steps, such as dispersion of active charcoal, filtration, distillation and the like, can also be included.

In another possible preparation process for the compounds according to the invention, epichlorohydrin is first reacted with the carboxylic acid of the formula V or with the phenol of the formula VI and the resulting intermediate is then reacted with the piperidine compound of the formula III, the epoxide ring being opened, to give the desired ester of the formula I or phenol ether of the formula II.

The compounds of the formulae I and II are suitable for stabilizing organic materials against thermal, oxidative and actinic degradation.

Examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium (III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals beeing elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

The invention therefore furthermore relates to compositions comprising (a) an organic material which is sensitive to oxidative, thermal and/or actinic degradation and (b) at least one compound of the formulae I and/or II, and to the use of compounds of the formulae I and II for stabilizing organic material against oxidative, thermal or actinic degradation. The invention also relates to a process for stabilizing organic material against thermal, oxidative and/or actinic degradation, which comprises adding at least one compound of the formulae I and/or II to this material.

The use of compounds of the formulae I and II as stabilizers in synthetic organic polymers is of particular interest.

The organic materials to be protected are preferably natural, semi-synthetic or, preferably, synthetic organic materials. Synthetic organic polymers or mixtures of such polymers, in particular thermoplastic polymers, such as polyolefins, especially polyethylene and polypropylene (PP), are particularly preferred. Coating compositions are also particularly preferred organic materials. Photographic materials are to be understood as meaning, in particular, the materials described in Research Disclosure 1990, 3 1429 (pages 474–480) for photographic reproduction and other reproduction techniques. Coating compositions which are advantageously to be stabilized in the context of the invention are described, for example, in Ullmann's Encyclopedia of Industrial Chemistry, 5th Edition, Volume A18, pages 359–464, VCH Verlagsgesellschaft, Weinheim 1991; such coating compositions often comprise further additives, for example those described below, in particular UV absorbers.

In general, the compounds of the formula I and/or II are added to the material to be stabilized in amounts of 0.01 to 10%, preferably 0.01 to 5%, in particular 0.01 to 2%, based on the total weight of the stabilized composition. The use of the compounds according to the invention in mounts of 0.05 to 1.5%, in particular 0.1 to 1.5%, is particularly preferred.

The incorporation into the materials can be carried out, for example, by mixing in or application of the compounds of the formula I and/or II and if appropriate further additives by the methods customary in the art. If the materials are polymers, in particular synthetic polymers, the incorporation can be carded out before or during shaping, or by application of the dissolved or dispersed compound to the polymer, if appropriate with subsequent evaporation of the solvent. In the case of elastomers, these can also be stabilized as latices. Another possibility for incorporation of the compounds of the formula I and/or II into polymers comprises addition of the compounds before, during or immediately after polymerization of the corresponding monomers or before crosslinking. The compound of the formula I can be added as such or in encapsulated form (for example in waxes, oils or polymers). In the case where the compounds of the formula I and/or II are added before or during the polymerization, they can also act as a regulator of the chain length of the polymers (chain stopper).

The compounds of the formula I and/or II can also be added to the plastics to be stabilized in the form of a masterbatch which comprises this compound, for example, in a concentration of 2.5 to 25% by weight.

The compounds of the formula I and/or II can advantageously be incorporated by the following methods:
- as an emulsion or dispersion (for example to latices or emulsion polymers),
- as a dry mixture during mixing of additional components or polymer mixtures,
- by direct addition into the processing apparatus (for example extruder, internal mixer and the like),
- as a solution or melt.

Polymer compositions according to the invention can be used or processed to various products in various forms, for example as (to) films, fibres, tapes, moulding compositions or profiles, or as binders for paints, adhesives or putty.

In addition to the compounds of the formula I and/or II, the compositions according to the invention can additionally comprise conventional additives, for example those defined below.

The conventional additives are advantageously employed in amounts of 0.1–10, for example 0.2–5% by weight, based on the polymer to be stabilized.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methyl-cyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tart-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-ten-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-tetramethylbenzene, 1,4-bis(3,5-di-tert-butyl-4-hydroxybenzyl)-2,3,5,6-tetramethylbenzene, 2,4,6-tris(3,5-di-ten-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxy-anilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β3-(5-tert-butyl-4-hydroxy-3-methylphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, ethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane. 1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane. 1.17. Amides of β-(3,5-di-tert-butyl-4-hydroxyphenyl)propionic acid e.g. N,N'-bis(3,5-di-tert-butyl-4-hydroxyphenylpropionyl) hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1.2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R-CH$_2$CH$_2$-COO(CH$_2$)$_3$-]$_2$, where R=3'-tert-butyl-4'-hydroxy-5'-2H-benzotriazol-2-ylphenyl.

2.2.2-Hydroxybenzophenones, for example the 4-hydroxy, 4-methoxy, 4-octyloxy, 4-decyloxy, 4-dodecyloxy, 4-benzyloxy, 4,2,4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol. 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-llauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, his(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione.

2.7. Oxamides, for example 4,4'-dioctyloxyoxanilide, 2,2'-diethoxyoxanilide, 2,2'-dioctyloxy-5,5'-di-tertbutoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, mines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4,316,611, DE-A-4,316,622, DE-A-4,316,876, EP-A-0,589,839 or EP-A-0,591,102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The examples which follow illustrate the invention further. In the examples, as in the remainder of the description and in the patent claims, all the parts or percentages are by weight, unless stated otherwise. The following abbreviations are used in the examples:

GC: Gas chromatography;

HPLC: High pressure liquid chromatography;

GPC: Gel permeation chromatography;

MALDI: Matrix Assisted Laser Desorption Ionization;

DSC: Differential thermal analysis;

DMF: Dimethylformamide;

THF: Tetrahydrofuran;

DMSO: Dimethyl sulfoxide;

Tg: Glass transition temperature;

$M_n$: Number-average molecular weight (units: g/mol);

$M_w$: Weight-average molecular weight (units: g/mol).

PREPARATION EXAMPLES (A, B)

A) Preparation of the epoxides

A1) Preparation of 1-benzyl-4-(2,3-epoxypropoxy)-2,2,6,6-tetramethylpiperidine 200 g of sodium hydroxide are dissolved in 200 ml of water in a 1.5 l sulfonation flask fitted with a glass stirrer, internal thermometer, dropping funnel and water condenser. 500 ml of toluene, 32.2 g (0.1 mol) of tetrabutylammonium bromide and 247.4 g (1 mol) of 1-benzyl-4-hydroxy-2,2,6,6-tetramethylpiperidine are then added.

185 g (2 mol) of epichlorohydrin are added dropwise at 50° C.–55° C., the mixture being stirred vigorously and the temperature then being kept at 55° C. for 2–3 hours, while stirring. The mixture is then poured onto 2 l of ice-water and extracted twice with 50 ml of ethyl acetate each time. The organic phase is dried and evaporated. The residue is distilled at 120° C. ($8\times10^3$ mmHg).

Yield: 165 g (54%) HPLC analysis: 96% purity

| | Microanalysis | |
|---|---|---|
| | calculated | found |
| C | 75.21 | 75.17 |
| H | 9.63 | 9.58 |
| N | 4.62 | 4.71 |

$^1$H-NMR (CDCl$_3$): 0.98 ppm and 1.11 ppm (12H,s): CH$_3$—; 1.44–1.54 ppm and 1.89–1.97 ppm (4H, m): —CH$_2$— of the piperidine ring; 2.62–2.64 ppm and 2.79–2.83 ppm (2H, m): $CH_2$ epoxide ring; 3.13–3.19 ppm (1H, m): CH epoxide ring; 3.45–3.51 and 3.77–3.81 ppm (2H, m): —O—$CH_2$—; 3.68–3.80 ppm (1H, m): —CH— of the piperidine ring; 3.81 ppm (2H, s): N—$CH_2$—; 7.11–7.43 ppm (5H, m): aromatic protons.

A2) Preparation of 1,2,2,6,6-pentamethyl-4-(2,3-epoxypropoxy)-piperidine 300 g of sodium hydroxide (7.5 mol) are dissolved in 300 ml of water under an argon atmosphere in a 2.5 l sulfonation flask with a mechanical stirrer, condenser and 500 ml dropping funnel. 750 ml of toluene, 48.4 g (0.15 mol) of tetrabutylammonium bromide and 257 g (1.5 mol) of 4-hydroxy-1,2,2,6,6-pentamethylpiperidine are added. 347 g of epichlorohydrin (3.75 mol) are added dropwise at 60° C. in the course of 1.5 hours and the temperature is then kept at 60° C. for a further 4 hours, while stirring. The reaction solution is poured onto 3 l of ice-water and the organic phase is separated off, dried with sodium sulfate and evaporated.

The residue is distilled over a Vigreux column under 0.05 mmHg and the fraction of boiling point 71°–72° C. is collected.

Yield: 205 g (60%), GC: >99%

| | Microanalysis | |
|---|---|---|
| | calculated | found |
| C | 68.68 | 68.64 |
| H | 11.07 | 11.21 |
| N | 6.16 | 6.32 |
| Cl | 0.0 | 0.0 |

$^1$H-NMR ($CDCl_3$): 1.02 and 1.16 ppm (12H, s): $CH_3$ groups of the piperidine ring; 1.32–1.4 ppm and 1.83–1.91 ppm (4H, m): —$CH_2$— groups of the piperidine ring; 2.23 ppm (3H, s): N—$CH_3$; 2.60–2.62 ppm and 2.78–2.82 ppm (2H, m): $CH_2$ group of the epoxide ring; 3.11–3.16 ppm (1H, m): CH of the epoxide ring; 3.42–3.47 and 3.71–3.76 ppm (2H, m): —O—$CH_2$— group; 3.57–3.67 ppm (1H, m): —CH—O of the piperidine ring;

A3) Preparation of 1-octyloxy-4-(2,3-epoxypropoxy)-2,2,6,6-tetramethylpiperidine 100 g of sodium hydroxide are dissolved in 100 ml of water in a 750 ml sulfonation flask with a glass stirrer, internal thermometer, dropping funnel and condenser. 71.4 g (0.25 mol) of 1-octyloxy-4-hydroxy-2,2,6,6-tetramethylpiperidine and 16.1 g (50 mmol) of tetrabutylammonium bromide are added.

The mixture is stirred vigorously at 30° C. A solution of 71.4 g (0.25 mol) of 1-octyloxy-4-hydroxy-2,2,6,6-tetramethylpiperidine in 277.5 g (3 mol) of epichlorohydrin is now added dropwise at 33°–35° C.

The mixture is stirred vigorously at 35° C. for 24 hours. It is poured onto 1l of ice-water and saturated with sodium chloride, and the organic phase is extracted with 500 ml of ethyl acetate and dried over sodium sulfate.

After the solvent has been evaporated off by a rotary evaporator, the residue is distilled at 130°–134° C. (0.01 mmHg).

Yield: 109.8 g (64%)

| | Microanalysis | |
|---|---|---|
| | calculated | found |
| C | 71.53 | 71.42 |
| H | 12.36 | 12.46 |
| N | 4.91 | 4.91 |

$^1$H-NMR ($CDCl_3$): 0.83–0.93 ppm (3H, m): $CH_3$ (octyl); 1.11–1.17 ppm (12H, m): $CH_3$ (piperidine); 1.28–1.81 ppm (18H, m): $CH_2$ (octyl, piperidine); 2.59–2.61 and 2.77–2.81 ppm (2H, m): $CH_2$ (epoxide ring); 3.10–3.14 ppm (1H, m): CH (epoxide ring); 3.32–3.44 and 3.68–3.72 ppm (2H, m): $CH_2$ (epoxide); 3.56–3.68 ppm (1H, m): CH (piperidine);

A4) Preparation of 2,2,6,6-tetramethyl-4-(2,3-epoxypropoxy)piperidine 64.0 g of sodium hydroxide (1.6 mol) are dissolved in 64 ml of water under argon in a 750 ml sulfonation flask with a mechanical stirrer, condenser, thermometer and 100 ml dropping funnel. 170 ml of toluene, 10.3 g (31.8 mmol) of tetrabutylammonium bromide and 50 g (318 mmol) of 4-hydroxy-2,2,6,6-tetramethylpiperidine are added.

58.8 g (636 mmol) of epichlorohydrin are added dropwise at 45° C. The mixture is then stirred at 50° C. for 4 hours. The reaction mixture is cooled to room temperature and poured onto 1 l of ice-water, and the organic phase is separated off, dried with sodium sulfate and concentrated on a rotary evaporator. The residue is distilled under $8 \times 10^3$ mmHg; boiling point: 48° C. 28 g (41% of theory) of the title product are obtained in a purity of 98% (GC).

| | Microanalysis | |
|---|---|---|
| | calculated | found |
| C | 67.57 | 67.73 |
| H | 10.87 | 10.92 |
| N | 6.57 | 6.51 |

H-NMR($CDCl_3$): 0.577 ppm (1H): NH; 0.81–0.98 ppm (2H, m): $CH_2$ (piperidine ring); 1.01 and 1.05 ppm (12H, s): $CH_3$ groups; 1.77–1.87 ppm (2H, m): $CH_2$ (piperidine ring); 2.47–2.50 and 2.66–2.69 ppm (2H, m): $CH_2$ (epoxide ring); 2.99–3.04 ppm (1H, m): CH (epoxide ring); 3.31–3.37 and 3.61–3.67 ppm (3H, m): $CH_2$ (epoxide) and CH—O (piperidine ring).

A5) 1-Cyclohexyloxy-2,2,6,6-tetramethyl-4-(2,3-epoxypropoxy)piperidine

A5a) 4-Acetyloxy-2,2,6,6-tetramethylpiperidine 786.5 g (5 mol) of 4-hydroxy-2,2,6,6-tetramethylpiperidine are initially introduced, under nitrogen, into a 10 l vessel with ground glass joints with a mechanical stirrer, thermometer, condenser and dropping funnel. 300 g (5 mol) of acetic acid and 1531 g (15 mol) of acetic anhydride are added. About 10 drops of concentrated sulfuric acid are slowly added dropwise and the mixture is stirred at 60° C. for 12 hours.

A solution of 1.2 kg of sodium oxide in 3 l of water is added at an internal temperature of less than 30° C.

The organic phase is extracted twice with 1 l of diethyl ether and dried over sodium sulfate and the solvent is evaporated off.

The substance is distilled under a waterpump vacuum: boiling point 103° C./15 mmHg.

Yield: 700 g (70%)

GC purity>95%

| Microanalysis | | |
|---|---|---|
| | calculated | found |
| C | 66.29 | 66.03 |
| H | 10.62 | 10.74 |
| N | 7.03 | 6.93 |

IR (KBr discs): C=O at 1740 cm$^{-1}$
$^1$H-NMR (CDCl$_3$): 1.03–1.18 ppm (2H,m): —CH$_2$—; 1.15 ppm (6H, s): CH$_3$—C; 1.24 ppm (6H, s): CH$_3$—C; 1.89–1.95 ppm (2H, m): —CH$_2$—; 2.03 ppm (3H, s): CH$_3$COO—;

A5b) 1-Cyclohexyloxy-2,2,6,6-tetramethyl-4-acetoxypiperidine 60 g (301 mol) of 4-acetoxy-2,2,6,6-tetramethylpiperidine are dissolved in 300 ml of cyclohexane under nitrogen in a 1.5 l sulfonation flask with a magnetic stirrer, water separator, thermometer and dropping funnel. 4.3 g (30 mmol) of molybdenum oxide are added.

154 g (1.2 mol) of an aqueous 70% solution of t-butyl hydroperoxide are extracted three times with 35 ml of cyclohexane each time and the organic phase is dried over sodium sulfate and transferred to the dropping funnel.

The reaction mixture is heated under reflux and the t-butyl hydroperoxide solution is added dropwise in the course of 2 hours. After a further 2 hours, the removal of water has ended. The mixture is kept at the reflux temperature overnight. It is then cooled to 25° C. and the catalyst is filtered off. Ice is added, a little sodium sulfite is added to destroy excess hydroperoxide and the organic phase is separated off. This is washed with water and dried over sodium sulfate and the solvent is removed on a rotary evaporator.

Yield: 85 g (95%)

The liquid is distilled in a bulb tube for analytical purposes. The colourless liquid boils at 115° C./0.05 mmHg.

GC analysis: 96%

| Microanalysis | | |
|---|---|---|
| | calculated | found |
| C | 68.65 | 68.57 |
| H | 10.51 | 10.49 |
| N | 4.71 | 4.56 |

$^1$H-NMR (CDCl$_3$): 1.19 ppm (12H, s): CH$_2$—C; 1.08–2.02 ppm (14H, m): —CH$_2$—; 2.01 ppm (3H, s): CH$_3$—COO; 4.95–5.05 ppm (1H, m):

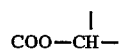

A5c) 1-Cyclohexyloxy-2,2,6,6-tetramethyl-4-hydroxypiperidine;

24 g (428 mmol) of potassium hydroxide are dissolved in 600 ml of methanol in a conical flask. 85 g (286 mmol) of 1-cyclohexyloxy-2,2,6,6-tetramethyl-4-acetoxypiperidine are poured into the warm solution, while stirring. The mixture is then poured onto ice and extracted with diethyl ether. After drying over sodium sulfate, the ether is evaporated off and the viscous residue is dissolved warm in 300 ml of acetonitrile. The solution is filtered and the filtrate is allowed to crystallize; yield: 50 g (68%).

The colourless substance has a melting point of 78.5° C.; purity according to GC analysis: 96%.

| Microanalysis | | |
|---|---|---|
| | calculated | found |
| C | 70.54 | 70.55 |
| H | 11.45 | 11.59 |
| N | 5.48 | 5.36 |

$^1$H-NMR (CDCl$_3$): 1.14 ppm and 1.24 ppm (12H, s): CH$_3$; 1.08–2.07 ppm (14H, m): —CH$_2$—; 3.57–3.62 ppm (1H, m): 4.95–5.05 ppm (1H, m):

3.90–3.99 ppm (1H, m):

A5d) 1-Cyclohexyloxy-2,2,6,6-tetramethyl-4-(2,3-epoxypropoxy)piperidine 78.4 g (1.96 mol) of sodium hydroxide are dissolved in 80 ml of water under argon in a 750 ml sulfonation flask fitted with a stirrer, thermometer and dropping funnel. 100 g (392 mmol) of 1-cyclohexyloxy-2,2,6,6-tetramethyl-4-hydroxypiperidine and 12.6 g (39.2 mmol) of tetrabutylammonium bromide, dissolved in 250 ml of toluene, are added. The mixture is heated to 50°–55° C., and 90.7 g (980 mmol) of epichlorohydrin are added dropwise in the course of 45 minutes. During this operation, the mixture is stirred vigorously.

The reaction mixture is stirred at 55° C. for a further 3 hours. It is then poured onto 1 litre of ice-water and the organic phase is separated off and washed once with water. The organic phase is dried over sodium sulfate, decolorized with active charcoal, filtered and evaporated.

The residue is distilled over a Vigreux column: boiling point 116°–117° C./0.06 mmHg.

Yield: 78.7 g (64%)
GC purity: 98%

| Microanalysis | | |
|---|---|---|
| | calculated | found |
| C | 69.41 | 69.34 |
| H | 10.68 | 11.24 |
| N | 4.50 | 4.39 |

$^1$H-NMR (CDCl$_3$): 1.13 ppm and 1.119 ppm (12H, s) CH$_3$—; 1.08 ppm–2.04 ppm (14H, m): —CH$_2$—; 2.59 ppm–2.81 ppm (2H, m): CH$_2$ epoxide ring; 3.10 ppm–3.43 ppm (2H, m): CH$_2$ epoxide; 3.56 ppm–3.73 ppm (3H, m): CH epoxide ring and CH—O of the six-membered rings.

Further epoxides are prepared analogously to the products A1 to A5 described above.

B) Preparation of the adducts

B1) Addition of bisphenol A onto epoxide A1

50 g (165 mmol) of epoxide A1, 17 g (75 mmol) of bisphenol A, 200 ml of xylene and 1.4 g (3.8 mmol) of ethyltriphenylphosphonium bromide are initially introduced into a 500 ml round-bottomed flask with a magnetic stirrer, condenser and argon bulb. The mixture is heated under reflux, while stirring, and the conversion is determined by HPLC.

After 15 hours, the mixture is poured onto ice and extracted with toluene. The organic phase is washed twice with water and dried over sodium sulfate. After evaporation, the product is chromatographed over silica gel 60 (manufacturer: E. Merck, Darmstadt) using hexane/ethyl acetate 2:1 and then dried under a high vacuum. The product of the formula

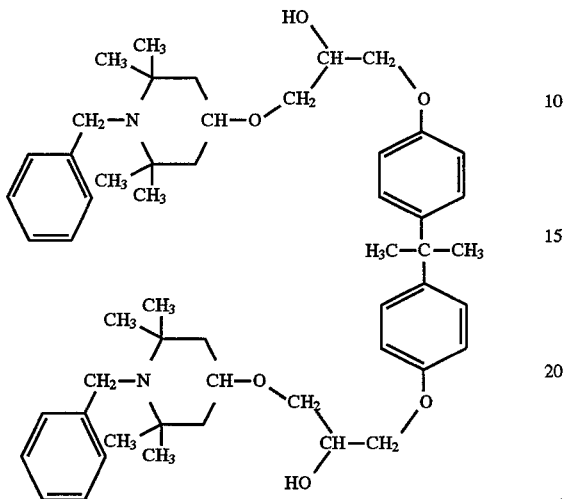

is obtained as a colourless, highly viscous liquid.

Yield: 37 g (59%)

| Microanalysis | calculated | found |
|---|---|---|
| C | 76.22 | 76.21 |
| H | 8.93 | 8.96 |
| N | 3.35 | 3.12 |

$^1$H-NMR (CDCl$_3$): 0.97 and 1.09 ppm (24H, s): CH$_3$ (piperidine); 1.44–1.52 ppm and 1.89–1.95 ppm (8H, m): CH$_2$ (piperidine); 1.68 ppm (6H, s): CH$_3$ (bisphenol A); 2.63–2.65 ppm (2H, d): OH; 3.60–3.75 ppm (6H, m): CH—O (piperidine) and CH$_2$—O-piperidine; 3.80 ppm (4H, s): N—CH$_2$—; 4.01–4.08 (4H, d),ar-O—CH$_2$; 4.10–4.16 (2H, m):

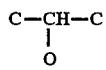

6.81–6.84 and 7.11–7.14 ppm (8H, m): H-ar (bisphenol A); 7.13–7.42 ppm (10H, m): H-ar (benzyl group).

No signals are visible in the range between 2.7 and 3.5 ppm, i.e. complete conversion of the epoxide groups has been achieved.

B2) Addition of resorcinol onto epoxide A2

100 g (440 mmol) of epoxide A2, 22 g (200 mmol) of resorcinol, 3.7 g (10 mmol) of ethyltriphenylphosphonium bromide and 400 ml of xylene are initially introduced into a 1 l round-bottomed flask with a magnetic stirrer, condenser and argon bulb.

The mixture is heated under reflux for 24 hours, while stirring. The cooled, clear solution is washed with 1N sodium hydroxide solution and with water and dried over sodium sulfate. After treatment with active charcoal, the solution is evaporated and the residue is dried under a high vacuum.

The product of the formula

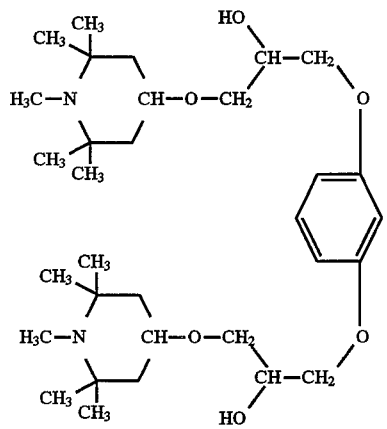

is obtained as a highly viscous clear liquid in quantitative yield.

| Microanalysis | calculated | found |
|---|---|---|
| C | 68.05 | 67.49 |
| H | 9.99 | 10.04 |
| N | 4.96 | 4.46 |

$^1$H-NMR (CDCl$_3$): no longer showns epoxide groups
GPC (THF):   M$_n$: 522
             M$_w$: 579

B3) 4-(3-Acryloxy-2-hydroxypropyloxy)-1,2,2,6,6-pentamethylpiperidine 375 g (1.65 mol) of 4-(2,3-epoxypropoxy)-1,2,2,6,6-pentamethylpiperidine in 1.5 l of xylene are initially introduced under argon into a 2.5 l sulfonation flask with a magnetic stirrer, thermometer and condenser. 108 g (1.5 mol) of acrylic acid and 27.8 g (75 mmol) of ethyltriphenylphosphonium bromide are added.

The mixture is allowed to react at 70° C. for 18 hours. The cooled product is poured onto ice-water and the organic phase is separated off. The organic phase is washed twice with 1N sodium hydroxide solution, dried and evaporated.

The residue is distilled over a short Vigreux column. 193 g (43%) of a clear liquid of boiling point 119°–125° C. (=0.06 mmHg) are obtained.

| Microanalysis | calculated | found |
|---|---|---|
| C | 64.18 | 63.50 |
| H | 9.76 | 9.76 |
| N | 4.68 | 4.67 |

$^1$H-NMR (CDCl$_3$): 1.02 and 1.16 ppm (12H, s): CH$_3$ (piperidine); 1.33–1.40 and 1.84–1.89 ppm (4H, m): CH$_2$ (piperidine); 2.23 ppm (3H, s): N—CH$_3$; 2.59 ppm (1H, s): OH; 3.46–3.63 and 3.71–3.72 and 3.84–3.86 and 3.98–4.05 and 4.18–4.29 ppm (6H,m):

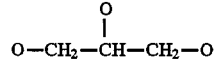

and CH (piperidine) 5.84–5.88 and 6.12–6.22 and 6.42–6.48 ppm (3H, m): CO—CH═CH$_2$.

B4) 4-(3-Methacryloxy-2-hydroxypropyloxy)-1,2,2,6,6-pentamethylpiperidine 250 g (1.1 mol) of 4-(2,3-epoxypropoxy)-1,2,2,6,6-pentamethylpiperidine are dissolved in 1 l of xylene under an inert gas in a 1.5 l sulfonation flask with a magnetic stirrer, thermometer and condenser. 86 g (1 mol) of methacrylic acid and 18.6 g (50 mmol) of ethyltriphenylphosphonium bromide are added.

The mixture is stirred at 70° C. for 18 hours. After cooling, it is poured onto ice-water and the organic phase is separated off. This is washed twice with 1N sodium hydroxide solution and dried. The solvent is evaporated off on a rotary evaporator and the residue is distilled under 0.07 mmHg.

176.5 g (56%) of a clear liquid which boils at 128°–130° C./0.07 mmHg are obtained.

| Microanalysis | | |
|---|---|---|
| | calculated | found |
| C | 64.14 | 64.72 |
| H | 9.97 | 10.00 |
| N | 4.47 | 4.33 |

$^1$H-NMR (CDCl$_3$): 1.01 and 1.16 ppm (12H, s): CH$_3$ (piperidine); 1.32–1.40 and 1.83–1.88 ppm (4H, m): CH$_2$ (piperidine); 1.96 ppm (3H, s): CH$_3$ (methacrylate); 2.23 ppm (3H, s): CH$_3$—N; 2.68 ppm (1H, s): OH; 3.46–4.26 ppm (6H, m):

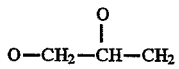

and CH (piperidine); 5.59 and 6.14 ppm (2H, s): CH$_2$=C.

B5) 4-(3-[4-Vinylbenzoyloxy]-2-hydroxypropyloxy)-1,2,2,6,6-pentamethylpiperidine 32.6 g (220 mmol) of 4-vinylbenzoic acid, 45.5 g (200 mmol) of 4-(2,3-epoxypropoxy)-1,2,2,6,6-pentamethylpiperidine, 3.7 g (10 mmol) of ethyltriphenylphosphonium bromide and 200 ml of xylene are initially introduced into a 500 ml round-bottomed flask fitted with a magnetic stirrer, condenser, thermometer and argon bulb.

The mixture is heated to 65° C. under an inert gas. The clear solution is kept at 65° C. for 15 hours and then poured onto ice. The organic phase is washed twice with 1N sodium hydroxide solution at 0° C., dried over sodium sulfate and evaporated.

The residue is purified over a silica gel column (THF) and dried under a high vacuum at 60° C.

52.7 g (70%) of a clear, viscous liquid are obtained.

| Microanalysis | | |
|---|---|---|
| | calculated | found |
| C | 70.37 | 69.89 |
| H | 8.86 | 9.22 |
| N | 3.73 | 3.79 |

$^1$H-NMR (CDCl$_3$): 1.01 and 1.15 ppm (12H, s): CH$_3$; 1.33–1.43 and 1.84–1.89 ppm (4H, m): CH$_2$ (piperidine); 2.23 ppm (3H, s): N—CH$_3$; 2.81 ppm (1H, s): OH; 3.42–4.40 ppm (6H, m):

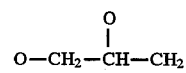

and CH (piperidine); 5.36–5.40 ppm and 5.83–5.89 ppm (2H, d): CH$_2$=; 6.70–6.79 ppm (1H, q): CH=; 7.44–7.47 ppm and 7.99–8.02 ppm (4H, d): aromatic.

B6) 4-(3-[4-vinylphenoxy]-2-hydroxypropyloxy)-1,2,2,6,6-pentamethylpiperidine 28.8 g (240 mmol) of 4-vinylphenol are reacted with 45.5 g (200 mmol) of 4-(2,3-epoxypropoxy)-1,2,2,6,6-pentamethylpiperidine analogously to Example B2).

Yield: 66 g (95%)

| Microanalysis: | % C | % H | % N |
|---|---|---|---|
| calculated | 72.58 | 9.57 | 4.03 |
| found | 72.67 | 9.53 | 3.89 |

$^1$H-NMR (CDCl$_3$): 1.01 and 1.15 ppm (12H, s): CH$_3$ (piperidine); 1.32–1.41 ppm and 1.84–1.89 ppm (4H, m): CH$_2$ (piperidine); 2.23 ppm (3H, s): N—CH$_3$; 2.72 ppm (1H, s): OH; 3.54–3.69 ppm (3H, m): pip-O—CH$_2$—CH—; 3.98–4.03 ppm (2H, d): ar-O—CH$_2$—; 4.06–4.12 ppm (1H, m):

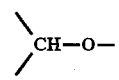

5.11–5.14 ppm und 5,58–5,64 ppm (2H, d): CH$_2$=; 6.60–6.70 ppm (1H, q): CH=; 6.86–6.89 ppm and 7.32–7.35 ppm (4H, d): H-aromatic.

EXAMPLES B7–B12

The adducts according to the following table are prepared by a method corresponding to that described under B3 by reaction of the corresponding epoxide with the corresponding acid:

| Example | Adduct | Epoxide | Acid |
|---|---|---|---|
| B7 | (structure: 4-vinylbenzoate ester of glycidyl-opened NOR-HALS adduct with cyclohexyloxy) | (structure: glycidyl ether of 2,2,6,6-tetramethyl-4-hydroxypiperidine N-O-cyclohexyl) | 4-vinylbenzoic acid (CH$_2$=CH–C$_6$H$_4$–COOH) |
| B8 | (structure: acrylate ester of glycidyl-opened NOR-HALS adduct with cyclohexyloxy) | (structure: glycidyl ether of 2,2,6,6-tetramethyl-4-hydroxypiperidine N-O-cyclohexyl) | acrylic acid (CH$_2$=CH–COOH) |
| B9 | (structure: methacrylate ester of glycidyl-opened NOR-HALS adduct with cyclohexyloxy) | (structure: glycidyl ether of 2,2,6,6-tetramethyl-4-hydroxypiperidine N-O-cyclohexyl) | methacrylic acid (CH$_2$=C(CH$_3$)–COOH) |

-continued

| Example | Adduct | Epoxide | Acid |
|---|---|---|---|
| B10 | 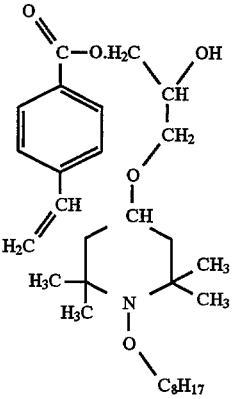 | 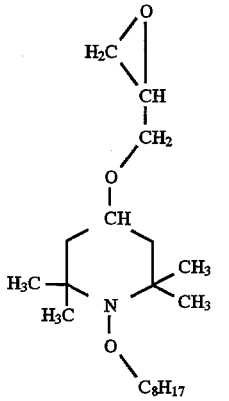 | 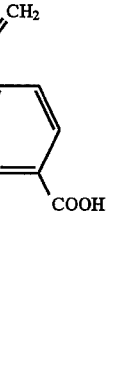 |
| B11 | 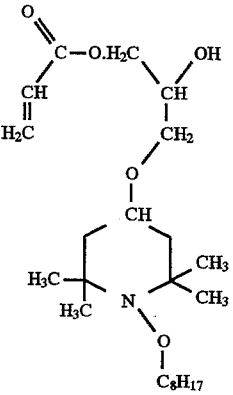 | 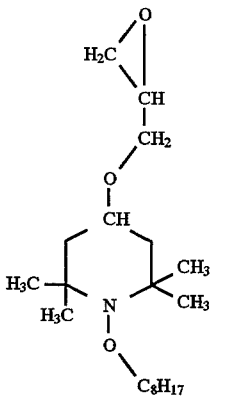 |  |
| B12 | 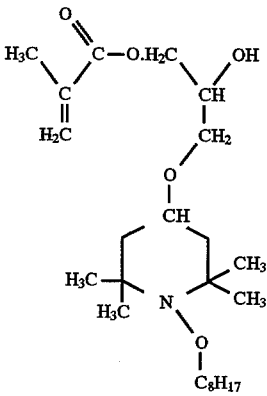 | 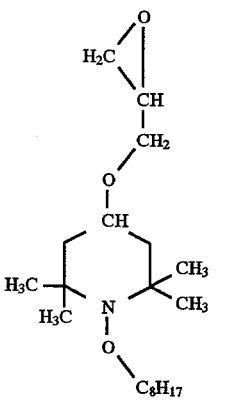 |  |

EXAMPLE B13

Bis[2-Hydroxypropyloxy-3-(1,2,2,6,6-pentamethylpiperid-4-yl)]isophthalate 100 g (440 mmol) of epoxide A2, 33 g (200 mmol) of isophthalic acid, 3.7 g (10 mmol) of ethyltriphenylphosphonium bromide and 400 ml of xylene are initially introduced under argon into a 1 l round-bottomed flask with a magnetic stirrer and reflux condenser.

The mixture is heated under reflux for 24 hours while stirring. It is then cooled to 0° C., and the solution is washed twice with 1N sodium hydroxide solution and once with water and dried over sodium sulfate. After treatment with active charcoal and filtration, the solution is evaporated on a rotary evaporator and the residue is dried under a high vacuum at 50° C.

The title product is obtained in quantitative yield; further data of the product are to be found in the following Table 1.

| Microanalysis | | |
|---|---|---|
| | calculated | found |
| C | 65.72 | 66.52 |
| H | 9.02 | 9.14 |
| N | 4.51 | 4.04 |

EXAMPLES B14–B25

The further adducts B14 to B25 listed in Table 1 are prepared by a method corresponding to that described in Examples B2 and B13.

Column 2 indicates the type of starting epoxide used and its molar ratio to the carboxylic acid or phenol used in the end product; for example 2xA2 in line 1 of Table 1 indicates that the compound of Example B 13 is the product of 2 mol of epoxide A2 per mol of isophthalic acid.

The abbreviations used in the table are

GPC: Results of the gel permeation chromatography $M_n$: Number-average molecular weight;

$M_w$: Weight-average molecular weight;

Tg: Glass transition temperature.

TABLE 1

Starting substances and physical data for the compounds of Examples 13–25.

| Ex. No. | Epoxide | (Carboxylic acid/ phenol) | Yield | GPC $M_n$ | $M_w$ | Product |
|---|---|---|---|---|---|---|
| B13 | 2 × A2 | Isophthalic acid | 100% | 672 | 897 | viscous liquid |
| B14 | 2 × A2 | Succinic acid | 23% | 680 | 910 | viscous liquid |
| B15 | 2 × A2 | Bisphenol A | 100% | 585 | 719 | viscous liquid |
| B16 | 2 × A2 | 1,4-Cyclohexane-dicarboxylic acid | 100% | 576 | 721 | solid, waxy |
| B17 | 1 × A2 | Stearic acid | 82% | 571 | 646 | viscous liquid |
| B18 | 2 × A2 | Sebacic acid | 92% | 692 | 861 | viscous liquid |
| B19 | 1 × A2 | Dodecanoic acid | 91% | 657 | 841 | viscous liquid |
| B20 | 1 × A2 | Lauric acid | 89% | 398 | 442 | viscous liquid |
| B21 | 2 × A1 | Sebacic acid | 96% | 737 | 948 | viscous liquid |
| B22 | 2 × A3 | Sebacic acid | 97% | 850 | 1093 | viscous liquid |
| B23 | 3 × A2 | Trimesic acid | 58% | 760 | 980 | solid Tg: 29° C. |
| B24 | 3 × A2 | Phloroglucinol | 81% | 900 | 1165 | solid Tg: 31° C. |
| B25 | 3 × A2 | 1,3,5-Cyclohexane-tricarboxylic acid | 62% | 750 | 850 | solid Tg: 20° C. |

B26) Adduct of 1,2,2,6,6-pentamethyl-4-(2,3-epoxypropoxy)piperidine and 1,2,4,5-benzenetetracarboxylic acid 10 g (39.3 mmol) of 1,2,4,5-benzenetetracarboxylic acid, 35.8 g (157.4 mmol) of 1,2,2,6,6-pentamethyl-4-(2,3-epoxypropoxy)piperidine (=epoxide A2) and 0.75 g (2 mmol) of ethyltriphenylphosphonium bromide are dissolved in 100 ml of DMSO and the solution is heated to 150° C. under argon. After 20 hours, the mixture is cooled to room temperature and poured onto water. It is extracted three times with ethyl acetate and the organic phase is washed with 1N sodium hydroxide solution. The organic phase is treated with active charcoal and sodium sulfate, filtered and evaporated. The residue is dissolved in a little ether and precipitated in n-hexane. 5.5 g of the title product are obtained as a pale beige powder; Tg=60°–65° C.

| Microanalysis: | C | H | N |
|---|---|---|---|
| calculated | 64.00 | 9.18 | 4.82 |
| found | 63.97 | 9.28 | 4.77 |

Molecular weight (MALDI): $M_n$=1800 $M_w$=2100

B27) 4-(3-[4-Vinylphenoxy]-2-hydroxypropyloxy)-1-cyclohexyloxy-2,2,6,6-tetramethylpiperidine 4-Vinylphenol is reacted with 4-(2,3-epoxypropoxy)-1-cyclohexyloxy-2,2,6,6-tetramethylpiperidine (=epoxide A5) analogously to Example B6) to form the title product.

B28) 4-(3-[4-Vinylphenoxy]-2-hydroxypropyloxy)-1-octyloxy-2,2,6,6-tetramethylpiperidine 4-Vinylphenol is reacted with 4-(2,3-epoxypropoxy)-1-octyloxy-2,2,6,6-tetra-methylpiperidine (=epoxide A3) analogously to Example B6) to form the title product.

C) USE EXAMPLES

EXAMPLE C1

Stabilization of polypropylene sheets

In each case 1 g of the stabilizer according to the invention shown in Table C1 is mixed with 1000 g of polypropylene of melt flow index 4.0 g/10 minutes (230° C.; 2.16 kg) from the manufacturer Statoil, Stathelle, Norway and the following additives:

0.5 g of pentaerythrityl tetrakis(3-[3',5'-di-tert-butyl-4'-hydroxyphenyl]propionate);

1.0 g of tris(2,4-di-tert-butyl-phenyl)phosphite;

1.0 g of FILOFIN® Blue G (pigment; Ciba Geigy S.p.A., Origgio, Italy);

1.0 g of calcium stearate.

For comparison purposes, a mixture is prepared without a stabilizer according to the invention.

The mixture is extruded at 200°–230° C. (Berstorff KE 30×32D). The resulting granules are processed to sheets 2 mm thick by the injection moulding process at 200°–220° C.

The sheets are exposed to light in accordance with ASTM D 2565-85 in a Weather-O-Meter® 65 WR (Arias Electric Devices, Chicago, USA) at a black panel temperature of 63°±3° C. The specimens are examined regularly; the start of superficial embrittlement (chalking) is determined. The exposure time before embrittlement occurs can be seen from the following Table C1.

TABLE C1

Exposure time to surface embrittlement

| Stabilizer from Example | Exposure time (hours) |
|---|---|
| none | 620 |
| B2 | 2810 |
| B13 | 2810 |
| B14 | 2810 |
| B15 | 2420 |
| B16 | 2810 |

The specimens stabilized according to the invention show an outstanding light stability.

EXAMPLE C2

Stabilization of a two-coat finish

A clearcoat is prepared from 54.5 parts of an acrylic resin (Uracron® 2263 XB, DSM Resin BV) (50% solution in xylene)

16.3 parts of a melamine resin (Cymel® 327, Amer. Cyanamid Co.) (90% solution)

19.4 parts of xylene 5.5 parts of butylglycol acetate 3.3 parts of butanol and 1.0 part of a flow auxiliary (Baysilon® A, Bayer AG) (1% solution in xylene).

The stabilizers according to the invention shown in Table C2 are added as a solution in xylene to the clearcoat in an amount of 1.0%, based on the solids content of the clearcoat. For comparison purposes, a sample is prepared without stabilizers. In addition to the stabilizer according to the invention, a UV absorber of the formula

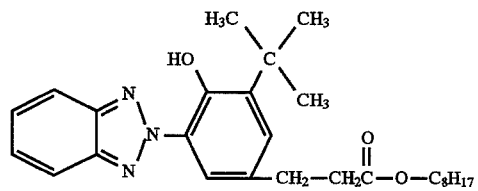

(=UVA) is also added to some of the samples in an amount of 1.5%, based on the solids content of the clearcoat.

The coating material samples thus prepared are diluted to spray viscosity with a mixture of xylene, butanol and butylglycol acetate (13:6:1) and sprayed onto a prepared aluminium panel (coil coat, automotive filler, silver-metallic basecoat). After storage for 15 minutes, the specimens are cured at 130° C. for 30 minutes. A clearcoat thickness of 40–50 µm results.

The specimens are then exposed to weathering in a UVCON weathering apparatus from Atlas (UVB-313 lamps) under a cycle of 8 hours UV irradiation at 70° C. and 4 hours condensation at 50° C. After in each case 400 hours of weathering, the 20° gloss of the specimens is measured in accordance with DIN 67530. The results are shown in Table C2.

EXAMPLE C3

Stabilization of a two-coat finish

The light stabilizers are incorporated into 5–10 g of xylene and tested in a clearcoat of the following composition:

| | |
|---|---|
| Synthacryl ® SC 303[1] | 27.51 |
| Synthacryl ® SC 370[2] | 23.34 |
| Maprenal ® MF 650[3] | 27.29 |
| Butyl acetate/butanol (37/8) | 4.33 |
| Isobutanol | 4.87 |
| Solvesso ® 150[4] | 2.72 |
| Kristallöl K-30[5] | 8.74 |
| Flow auxiliary Baysilon ® MA[6] | 1.20 |
| | 100.00 g |

[1] Acrylate resin, Hoechst AG; 65% solution in xylene/butanol 26:9
[2] Acrylate resin, Hoechst AG; 75% solution in Solvesso ® 100[4]
[3] Melamine resin, Hoechst AG; 55% solution in isobutanol
[4] Manufacturer: ESSO
[5] Manufacturer: Shell
[6] 1% in Solvesso ® 150; manufacturer: Bayer AG 1% of stabilizer, based on the solids content of the coating material, are added to the clearcoat. A clear lacquer which contains no light stabilizer is used for comparison.

The clearcoat is diluted to spray viscosity with Solvesso® 100 and sprayed onto a prepared aluminium sheet (coil coat, filler, silver-metallic basecoat) and stoved at 130° C. for 30 minutes. A dry film thickness of 40–50 µm of clearcoat results.

The specimens are then exposed to weathering in an UVCON® weathering apparatus from Atlas Corp. (UVB-313 lamps) under a cycle of 4 hours UV irradiation at 60° C. and 4 hours condensation at 50° C.

The specimens are examined for cracks at regular intervals of time. The results are shown in Table C3.

TABLE C2

20° gloss in accordance with DIN 67530 after the stated weathering time

| Stabilizer | 0 hours | 1200 hours | 2400 hours | 3600 hours | 4800 hours | 6000 hours | 7200 hours |
|---|---|---|---|---|---|---|---|
| none | 87 | 45 | 26 | * | * | * | * |
| from B18 | 87 | 81 | 48 | 38 | 25 | * | * |
| from B19 | 87 | 78 | 36 | 30 | 17 | * | * |
| from B22 | 87 | 73 | 37 | 30 | 18 | * | * |
| from B18 + UVA | 87 | 85 | 83 | 83 | 81 | 80 | 73 |
| from B19 + UVA | 87 | 86 | 83 | 83 | 82 | 81 | 79 |
| from B21 + UVA | 87 | 84 | 82 | 80 | 79 | 75 | 67 |
| from B22 + UVA | 87 | 86 | 83 | 83 | 82 | 80 | 77 |

*Specimen matt or shrunken

The specimens with the stabilizers according to the invention show an outstanding gloss retention.

TABLE C3

| Stabilizer | Weathering time to cracking<br>Cracking after |
|---|---|
| none | 1200 hours |
| from Example B23 | >4800 hours |

The specimen with the stabilizer according to the invention shows a high resistance to cracking.

EXAMPLE C4

Stabilization of a photographic material 0.087 g of the yellow coupler of the formula

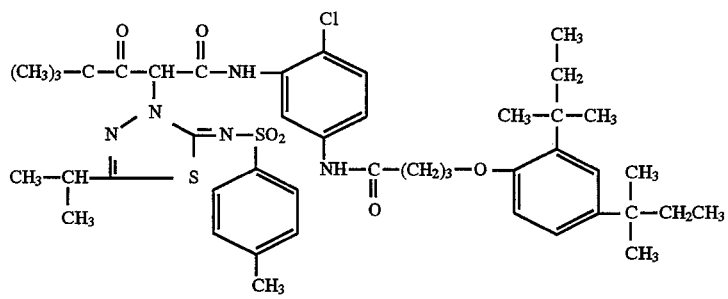

is dissolved in 2.0 ml of a solution of the stabilizer according to the invention in ethyl acetate (2.25 g/100 ml). 9.0 ml of a 2.3% aqueous gelatin solution which has been brought to a pH of 6.5 and comprises 1.744 g/l of the wetting agent of the formula

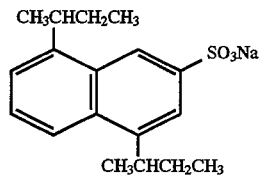

are added to 1.0 ml of this solution.

2 ml of a silver.bromide emulsion having a silver content of 6.0 g/l and 1.0 ml of a 0.7% aqueous solution of the hardener of the formula

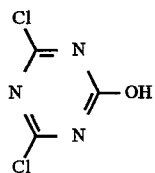

are added to 5.0 ml of the coupler emulsion thus obtained and the mixture is poured onto a 13×18 cm plastic-coated paper. After a hardening time of 7 days, the specimens are exposed to light behind a silver step wedge at 125 lux.s and then processed by the Ektaprint 2® process of Kodak.

The resulting yellow wedges are irradiated in an Atlas Weather-O-Meter with a 2500 W xenon lamp behind a UV filter (Kodak 2C) with a total of 60 k joules/cm².

A specimen without a stabilizer is also run as a standard.

The loss in colour density at the absorption maximum of the yellow dye which has occurred during irradiation is measured with a TR 924A densitometer from Macbeth.

The light stabilizing effect can be seen from the loss in colour density. The smaller the loss in density, the higher the light stabilizing activity.

The stabilizers according to the invention show a good light stabilizing action.

What is claimed is:

1. A composition comprising

A) an organic material which is sensitive to oxidative, thermal and/or actinic degradation; and B) an effective stabilizing amount of a compound of the formula I

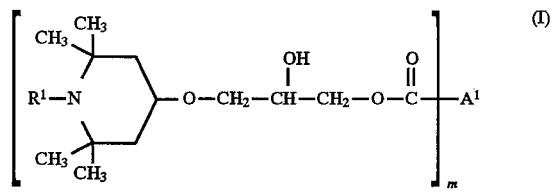

or a compound of the formula II

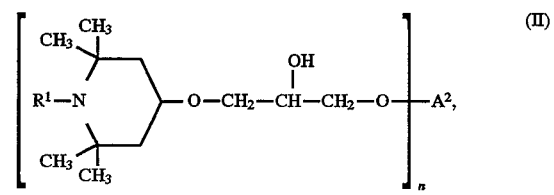

in which m and n are each an integer from the range from 1 to 6;

$A^1$ is an m-valent hydrocarbon radical having 1 to 30 carbon atoms; or an m-valent hydrocarbon radical having 2 to 30 carbon atoms, which contains a heteroatom selected from oxygen, nitrogen and sulfur, and m free valencies of which being located on carbon atoms; and in which $A^1$, in the case where m=2, additionally is a direct bond;

$A^2$ is an n-valent aromatic or araliphatic hydrocarbon radical having 6 to 30 carbon atoms; or an n-valent aromatic or araliphatic hydrocarbon radical having 5 to 30 carbon atoms, which contains a heteroatom selected from oxygen, nitrogen and sulfur, and n free valencies of which are located on those carbon atoms which are a constituent of aromatic rings in which $A^2$, in the case where n=1, is phenyl, which is unsubstituted or substituted by 1 to 3 radicals selected from the group consisting of $C_1$–$C_4$alkyl, $C_2$–$C_4$alkenyl, $C_1$–$C_4$alkoxy and a radical of the formula

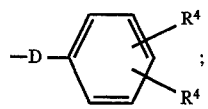

a triazinylphenyl radical of the formula

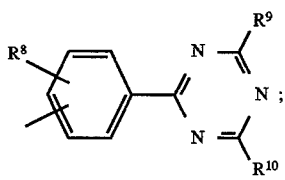

or naphthyl;

where D is a direct bond, $C_1$–$C_{10}$alkylene, or one of the groups —CO—, —S—, —O— or —SO$_2$—, $R^4$ and $R^{4'}$ independently of one another are hydrogen or $C_1$–$C_4$alkyl, $R^6$ is hydrogen or $C_1$–$C_4$alkyl, and $R^9$ and $R^{10}$ independently of one another are $C_3$–$C_{18}$alkyl or $C_3$–$C_{18}$cycloalkyl, and $A^2$, in the case where n is 2–6, is an n-valent aromatic or aliphatic hydrocarbon radical having 6 to 30 carbon atoms; or an n-valent aromatic or araliphatic hydrocarbon radical having 5 to 30 carbon atoms, which contains a heteratom selected from oxygen, nitrogen and sulfur, and n free valencies of which are located on those carbon atoms which are a constituent of aromatic rings;

$R^1$ is hydrogen; a hydrocarbon or hydrocarbonoxy radical having 1 to 36 carbon atoms, which is unsubstituted or substituted by —CO—N($R^3$)$_2$ or interrupted by —CO—N($R^3$)— or —N($R^3$)—CO— or 1 to 6 oxygen or sulfur atoms; benzoyl or naphthoyl, each of which is substituted by 1 to 3 $C_1$–$C_4$alkyl or $C_1$–$C_4$alkoxy radicals; or —CO—$R^2$; in which $R^2$ is $C_1$–$C_{18}$alkyl; $C_5$–$C_8$cycloalkyl; phenyl; naphthyl; $C_7$–$C_9$phenylalkyl; or $C_{11}$–$C_{14}$naphthylalkyl; and $R^3$ has the same meanings as $R^2$ or is hydrogen.

2. A composition according to claim 1 comprising

A) an organic material which is sensitive to oxidative, thermal and/or actinic degradation; and B) an effective stabilizing amount of a compound of the formula I

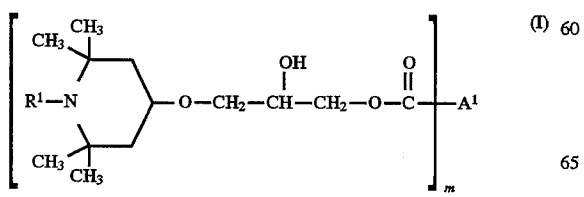

or a compound of the formula II

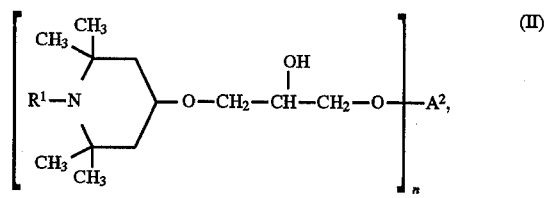

in which m and n are each an integer from the range from 1 to 6;

$A^1$ is an m-valent hydrocarbon radical having 1 to 30 carbon atoms; or an m-valent hydrocarbon radical having 2 to 30 carbon atoms, which contains a heteroatom selected from oxygen, nitrogen and sulfur, and m free valencies of which being located on carbon atoms; and in which $A^1$, in the case where m=2, additionally is a direct bond;

$A^2$ is an n-valent aromatic or araliphatic hydrocarbon radical having 6 to 30 carbon atoms; or an n-valent aromatic or araliphatic hydrocarbon radical having 5 to 30 carbon atoms, which contains a heteroatom selected from oxygen, nitrogen and sulfur, and n free valencies of which are located on those carbon atoms which are a constituent of aromatic rings in which $A^2$, in the case where n=1, is phenyl, which is unsubstituted or substituted by 1 to 3 radicals selected from the group consisting of $C_1$–$C_4$alkyl, $C_2$–$C_4$alkenyl, $C_1$–$C_4$alkoxy and a radical of the formula

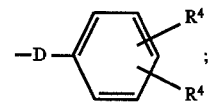

a triazinylphenyl radical of the formula

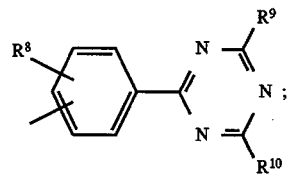

or naphthyl;

where D is a direct bond, $C_1$–$C_{10}$alkylene, or one of the groups —CO—, —S—, —O— or —SO$_2$—, $R^4$ and $R^{4'}$ independently of one another are hydrogen or $C_1$–$C_4$alkyl, $R^6$ is hydrogen or $C_1$–$C_4$alkyl, and $R^9$ and $R^{10}$ independently of one another are $C_3$–$C_{18}$alkyl or $C_3$–$C_8$cycloalkyl, and $A^2$, in the case where n=2, is phenylene, which is unsubstituted or substituted by 1 or 2 $C_1$–$C_4$alkyl, $C_2$–$C_4$alkenyl or $C_1$–$C_4$alkoxy radicals and/or a group of the formula

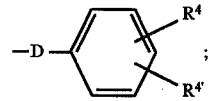

a divalent radical of the formula

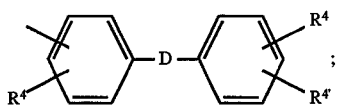

or naphthylene;

$A^2$, in the case where n=3, is benzenetriyl; or a trivalent radical of the formula

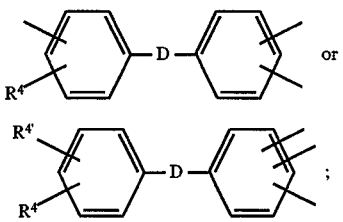

$A^2$, in the case where n=4, is a benzene radical having 4 free valencies or a tetravalent radical of the formula

or $A^2$ is an n-valent triphenyltriazinyl radical of the formula

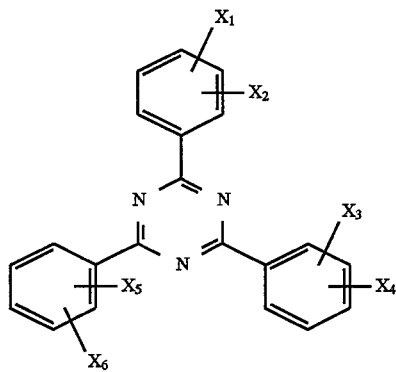

in which 1 to 4 of the radicals $X_1$ to $X_6$ in each case are an open bond and the others, independently of one another, are hydrogen or $C_1$–$C_4$alkyl;

D is a direct bond; $C_1$–$C_{10}$alkylene; or one of the groups —CO—, —S—, —O— or —$SO_2$—;

$R^1$ is $C_1$–$C_{36}$alkyl; $C_3$–$C_{36}$alkenyl; $C_3$–$C_9$alkynyl; $C_1$–$C_{36}$alkoxy; $C_3$–$C_{36}$alkenyloxy; $C_5$–$C_{12}$cycloalkyl, which is unsubstituted or substituted by 1 to 3 $C_1$–$C_4$alkyl or $C_1$–$C_4$alkoxy radicals; $C_5$–$C_{12}$cycloalkoxy, which is unsubstituted or substituted by 1 to 3 $C_1$–$C_4$alkyl or $C_1$–$C_4$alkoxy radicals; phenyl, which is unsubstituted or substituted by 1 to 3 $C_1$–$C_4$alkyl or $C_1$–$C_4$alkoxy radicals; naphthyl, which is unsubstituted or substituted by 1 to 3 $C_1$–$C_4$alkyl or $C_1$–$C_4$alkoxy radicals; phenoxy, which is unsubstituted or substituted by 1 to 3 $C_1$–$C_4$alkyl or $C_1$–$C_4$alkoxy radicals; naphthoxy, which is unsubstituted or substituted by 1 to 3 $C_1$–$C_4$alkyl or $C_1$–$C_4$alkoxy radicals; $C_7$–$C_{12}$phenylalkyl, which is unsubstituted or substituted on the phenyl ring by 1 to 3 $C_1$–$C_4$alkyl or $C_1$–$C_4$alkoxy radicals; $C_7$–$C_{12}$phenylalkoxy, which is unsubstituted or substituted on the phenyl ring by 1 to 3 $C_1$–$C_4$alkyl or $C_1$–$C_4$alkoxy radicals; or —CO—$R^2$; in which $R^2$ is $C_1$–$C_{18}$alkyl; $C_5$–$C_8$cycloalkyl; phenyl; naphthyl; $C_7$–$C_9$phenylalkyl; or $C_{11}$–$C_{14}$naphthylalkyl; and $R^3$ has the same meanings as $R^2$ or is hydrogen;

$R^4$ and $R^{4'}$ independently of one another are hydrogen or $C_1$–$C_4$alkyl;

$R^5$, $R^6$ and $R^7$ independently of one another are $C_1$–$C_3$alkylene;

$R^8$ is hydrogen or $C_1$–$C_4$alkyl;

$R^9$ and $R^{10}$ independently of one another are $C_3$–$C_{18}$alkyl or $C_5$–$C_8$cycloalkyl; and $R^{11}$ is $C_2$–$C_6$alkylene.

3. A composition according to claim 1, in which the organic material is a synthetic organic polymer or a mixture of synthetic organic polymers.

4. A composition according to claim 3, in which component A is a coating composition.

5. A composition according to claim 1, which comprises component B in an amount of 0.01 to 10%, based on the total weight of the stabilized composition.

6. A composition according to claim 1, which additionally comprises as component C a conventional additive, in addition to components A and B.

* * * * *